(12) United States Patent
Har-Noy

(10) Patent No.: US 10,350,242 B2
(45) Date of Patent: Jul. 16, 2019

(54) METHODS FOR HANDLING BIOLOGICAL DRUGS CONTAINING LIVING CELLS

(75) Inventor: Michael Har-Noy, Jerusalem (IL)

(73) Assignee: IMMUNOVATIVE THERAPIES LTD., Jerusalem (IL)

( * ) Notice: Subject to any disclaimer, the term of this patent is extended or adjusted under 35 U.S.C. 154(b) by 0 days.

(21) Appl. No.: 13/581,895

(22) PCT Filed: May 2, 2012

(86) PCT No.: PCT/US2012/036103
§ 371 (c)(1),
(2), (4) Date: Nov. 9, 2012

(87) PCT Pub. No.: WO2012/151266
PCT Pub. Date: Nov. 8, 2012

(65) Prior Publication Data
US 2013/0101562 A1    Apr. 25, 2013

Related U.S. Application Data

(60) Provisional application No. 61/481,991, filed on May 3, 2011, provisional application No. 61/528,493, filed on Aug. 29, 2011, provisional application No. 61/565,225, filed on Nov. 30, 2011, provisional application No. 61/582,878, filed on Jan. 4, 2012.

(51) Int. Cl.
*A61K 35/17* (2015.01)
*B65B 1/04* (2006.01)
*A61K 38/21* (2006.01)

(52) U.S. Cl.
CPC ............ *A61K 35/17* (2013.01); *A61K 38/217* (2013.01); *B65B 1/04* (2013.01)

(58) Field of Classification Search
None
See application file for complete search history.

(56) References Cited

U.S. PATENT DOCUMENTS

| | | | |
|---|---|---|---|
| 4,279,249 A | 7/1981 | Vert et al. | |
| 5,126,132 A | 6/1992 | Rosenberg | |
| 5,443,983 A | 8/1995 | Ochoa et al. | |
| 5,766,920 A | 6/1998 | Babbitt et al. | |
| 5,806,529 A | 9/1998 | Reisner et al. | |
| 5,846,827 A | 12/1998 | Celis et al. | |
| 6,040,177 A | 3/2000 | Riddell et al. | |
| 6,194,207 B1 | 2/2001 | Bell et al. | |
| 6,251,385 B1 | 6/2001 | Terman | |
| 6,255,073 B1 | 7/2001 | Cai et al. | |
| 6,352,694 B1 | 3/2002 | June et al. | |
| 6,500,193 B1 | 12/2002 | Bezemer et al. | |
| 6,511,511 B1 | 1/2003 | Slivka et al. | |
| 6,514,286 B1 | 2/2003 | Leatherbury et al. | |
| 6,534,055 B1 | 3/2003 | June et al. | |
| 6,572,894 B2 | 6/2003 | Rossling et al. | |
| 6,867,041 B2 | 3/2005 | Berenson et al. | |
| 6,887,466 B2 | 5/2005 | June et al. | |
| 6,905,680 B2 | 6/2005 | June et al. | |
| 6,905,681 B1 | 6/2005 | June et al. | |
| 6,905,874 B2 | 6/2005 | Berenson et al. | |
| 7,402,431 B2 | 7/2008 | Har-Noy | |
| 7,435,592 B2 | 10/2008 | Har-Noy | |
| 7,678,572 B2 | 3/2010 | Har-Noy | |
| 2002/0127208 A1 | 9/2002 | Waller et al. | |
| 2003/0004578 A1 | 1/2003 | Brown et al. | |
| 2003/0170238 A1* | 9/2003 | Gruenberg ........... A61K 39/395 | 424/144.1 |
| 2003/0175272 A1 | 9/2003 | Gruenberg | |
| 2003/0215946 A1 | 11/2003 | Nair et al. | |
| 2004/0228848 A1* | 11/2004 | Har-Noy ................. 424/93.71 | |
| 2005/0065593 A1 | 3/2005 | Chu et al. | |
| 2005/0191746 A1 | 9/2005 | Van et al. | |
| 2006/0036331 A1 | 2/2006 | Lu et al. | |
| 2006/0121021 A1 | 6/2006 | Hunig | |
| 2007/0086996 A1 | 4/2007 | Har-Noy | |
| 2009/0274765 A1* | 11/2009 | Beduneau et al. ............ 424/490 | |

FOREIGN PATENT DOCUMENTS

| | | |
|---|---|---|
| EP | 0319012 A2 | 6/1989 |
| EP | 1480519 A1 | 12/2004 |
| EP | 1594989 A2 | 11/2005 |
| EP | 1792979 A1 | 6/2007 |
| JP | 2001509135 A | 7/2001 |
| JP | 2009501526 A | 1/2009 |
| WO | 9412196 A1 | 6/1994 |
| WO | 9746256 A1 | 12/1997 |
| WO | 9924045 A1 | 5/1999 |
| WO | 200162895 A2 | 8/2001 |
| WO | 2003024989 | 3/2003 |
| WO | 03077658 | 9/2003 |
| WO | 2003038062 | 10/2003 |
| WO | 2004004768 A1 | 1/2004 |
| WO | 2005001074 A | 1/2005 |
| WO | 2005001074 A1 | 1/2005 |
| WO | 2005081982 A | 9/2005 |
| WO | 2005084276 A | 9/2005 |

OTHER PUBLICATIONS

Hollyman et al. (J lmmunother 2009;32:169-180).*
Brentjens et al. (Clin Cancer Res 2007;13:5426-5435).*
Kalamasz et al. (Blood, Nov. 16, 2000, vol. 96, No. 11 Part 2, p. 316b).*
Jones et al. (Cold-Chain Logistics: A Study of the Department of the Defense Oconus Pre-Pandemic Vaccine Distribution Network, Naval Postgraduate School, Dec. 2007, pp. i-xvi and 1-57).*
Whiteside et al. (Cytotherapy, Feb. 2011; 13: 201-213, Epub Aug. 26, 2010).*

(Continued)

*Primary Examiner* — Zachary S Skelding
(74) *Attorney, Agent, or Firm* — Westman, Champlin & Koehler, P.A.; Z. Peter Sawicki; Visala C. Goswitz

(57) ABSTRACT

The present invention includes methods for handling live cell compositions in non-nutritive buffer. The cells in the compositions maintain their identity and functional characteristics after being stored in non-nutrititive media up to about 72 hours. The storage method enables the cells to be manufactured at a processing facility and shipped to a point of care site. The invention also includes compositions that have been stored in non-nutritive buffer at storage temperatures while maintaining the functional characteristics.

14 Claims, 18 Drawing Sheets

(56) References Cited

OTHER PUBLICATIONS

Kao et al. (Transfusion. Jan. 2011;51(1):137-47).*
DiGiusto et al., Cytotherapy (2007) vol. 9, No. 7, 613-629.*
Jeurink et al., Cryobiology 57 (2008) 91-103.*
Dynabeads anti-CD3/CD28, 2006, pp. 1-8.*
Waybackmachine, http://web.archive.org/web/20110624115746/http://simple.wikipedia.org/wiki/Room_temperature, pp. 1-2.*
Lancioni et al., J Immunol Methods. May 15, 2009; 344(1): 15-25 (Year: 2009).*
Leitner et al., Immunology Letters 128 (2010) 89-97 (Year: 2010).*
Smith-Garvin et al., Annu. Rev. Immunol. 2009. 27:591-619 (Year: 2009).*
Antin, J. H. et al. (1992). "Cytokine Dysregulation and Acute Graft-Versus-Host Disease." Blood, vol. 80, No. 12: pp. 2964-2968.
Anderson, P. et al. (1988). "Crosslinking CD3 with CD2 Using Sepharose-Immobilized Antibodies Enhances T Lymphocyte Proliferation." Cellular Immunology, vol. 115, No. 2: pp. 246-256.
Asselin-Paturel et al. (1998). "Quantitative Analysis of Th1, Th2 and TGF-β1 Cytokine Expression in Tumor, TIL and PBL of Non-Small Cell Lung Cancer Patients." Int. J. Cancer, vol. 77, No. 1: pp. 7-12.
Bachmann, M. F. et al. (1997). "Distinct Roles for LFA-1 and CD28 During Activation of Naive T Cells: Adhesion Versus Costimulation." Immunity, vol. 7, No. 4: pp. 549-557.
Banu, N. et al. (1999). "TGF-β1 down-regulates induced expression of both class II MHC and B7-1 on primary murine renal tubular epithelial cells." Kidney International, vol. 56, No. 3: pp. 985-994.
Baroja, M.L. et al. (1989). "The Anti-T Cell Monoclonal Antibody 9.3 (Anti-CD28) Provides a Helper Signal and Bypasses the Need for Accessory Cells in T Cell Activation with Immobilized Anti-CD3 and Mitogens." Cellular Immunology, vol. 120, No. 1: pp. 205-217.
Baxevanis, C. N. et al. (2000). "Compromised anti-tumor responses in tumor necrosis factor-α knockout mice." Eur. J. Immunol., vol. 30, No. 7: pp. 1957-1966.
Belardelli, F. et al. (2002). "Cytokines as a link between innate and adaptive antitumor immunity." Trends in Immunology, vol. 23 No. 4: pp. 201-208.
Blazar, B. R. et al. (1997). "Recent advances in graft-versus-host disease (GVHD) prevention." Immunological Reviews, vol. 157: pp. 79-109.
Blazar, B. R. et al. (1998). "Rapamycin Inhibits the Generation of Graft-Versus-Host Disease- and Graft-Versus-Leukemia-Causing T Cells by Interfering with the Production of Th1 or Th1 Cytotoxic Cytokines." Journal of Immunology, vol. 160, No. 11: pp. 5355-5365.
Carayol, G. et al. (1997). "Quantitative Analysis of T Helper 1, T Helper 2, and Inflammatory Cytokine Expression in Patients After Allogeneic Bone Narrow Transplantation: Relationship with the Occurrence of Acute Graft-Versus-Host Disease." Transplantation, vol. 63, No. 9: pp. 1307-1313.
Carpentier, A. F., G. Auf, et al. (2003). "CpG-oligonucleotides for cancer immunotherapy : review of the literature and potential applications in malignant glioma." Front Biosci 8: E115-27.
Chambers, C. A. et al. (1999). "Costimulatory regulation of T cell function." Current Opinion in Cell Biology, vol. 11, No. 2: pp. 203-210.
Champlin, R., I. Khouri, et al. (1999). "Allogeneic hematopoietic transplantation as adoptive immunotherapy. Induction of graft-versus-malignancy as primary therapy." Hematol Oncol Clin North Am 13(5): 1041-57, vii-viii.
Champlin, R., K. van Besien, et al. (2000). "Allogeneic hematopoietic transplantation for chronic lymphocytic leukemia and lymphoma: potential for nonablative preparative regimens." Curr Oncol Rep 2(2): 182-91.
Chang, J. W., M. Peng, et al. (2000). "Induction of Th1 response by dendritic cells pulsed with autologous melanoma apoptotic bodies." Anticancer Res 20(3A): 1329-36.

Chen, Q. et al. (1994). "Production of IL-10 by Melanoma Cells: Examination of its Role in Immunosuppression Mediated by Melanoma." Int. J. Cancer, vol. 56, No. 5: pp. 755-760.
Childs, R. et al. (2002). "Nonmyeloablative Stem Cell Transplantation for Solid Tumors: Expanding the Application of Allogeneic Immunotherapy." Seminars in Hematology, vol. 39, No. 1: pp. 63-71.
Childs, R. et al. (2000). "Regression of metastatic renal-cell carcinoma after nonmyeloablative allogeneic peripheral-blood stem-cell transplantation." The New England Journal of Medicine, vol. 343, No. 11: pp. 750-758.
Childs, R. W. (2000). "Nonmyeloablative allogeneic peripheral blood stem-cell transplantation as immunotherapy for malignant diseases." Cancer J 6(3): 179-87.
Childs, R. W. (2002). "Immunotherapy of solid tumors: nonmyeloablative allogeneic stem cell transplantation." MedGenMed 4(3): 13.
Clerici , M. et al. (1993). "A TH1→TH2 switch is a critical step in the etiology of HIV infection." Immunology Today, vol. 14, No. 3: pp. 107-111.
Cohen, P. A., L. Peng, et al. (2000). "CD4+ T cells in adoptive immunotherapy and the indirect mechanism of tumor rejection." Crit Rev Immunol 20(1): 17-56.
Damle, N.K. et al. (1989). "Stimulation Via the CD3 and CD28 Molecules Induces Responsiveness to IL-4 in CD4 +CD29+CD45R- Memory T Lymphocytes." The Journal of Immunology, vol. 143, No. 6: pp. 1761-1767.
Das, H., S. Imota, et al. (2001). "Kinetic analysis of cytokine gene expression in patients with GVHD after donor lymphocyte infusion." Bone Marrow Transplant 27(4): 373-80.
Daubener, W. et al. (1995). "Establishment of T-helper type 1- and T-helper type 2-like human Toxoplasma antigen-specific T-cell clones." Immunology, vol. 86, No. 1: pp. 79-84.
Deeths, M. J. et al. (1999). "CD8+ T Cells Become Nonresponsive (Anergic) Following Activation in the Presence of Costimulation." The Journal of Immunology, vol. 163, No. 1: pp. 102-110.
De Vita, F., M. Orditura, et al. (2000). "Serum interleukin-10 is an independent prognostic factor in advanced solid tumors." Oncol Rep 7(2): 357-61.
de Waal Malefyt, R. et al. (1993). "Direct Effects of IL-10 on Subsets of Human CD4+ T Cell Clones and Resting T Cells. Specific Inhibition of IL-2 Production and Proliferation." The Journal of Immunology, vol. 150, No. 11: pp. 4754-4765.
D'Orazio, T. J. et al. (1998). "A Novel Role for TGF-β and IL-10 in the Induction of Immune Privilege." The Journal of Immunology, vol. 160, No. 5: 2089-2098.
Dudley, M. E. et al. (2002), "Cancer Regression and Autoimmunity in Patients After Clonal Repopulation with Antitumor Lymphocytes." Science, vol. 298, No. 5594: pp. 850-854.
Egeter, O. et al. (2000). "Eradication of Disseminated Lymphomas with CpG-DNA Activated T Helper Type 1 Cells from Nontransgenic Mice." Cancer Research, vol. 60, No. 6: 1515-1520.
Eibl, B. et al. (1996). "Evidence for a Graft-Versus-Tumor Effect in a Patient Treated With Marrow Ablative Chemotherapy and Allogeneic Bone Marrow Transplantation for Breast Cancer." Blood, vol. 88, No. 4: pp. 1501-1508.
Elsasser-Beile, U. et al. (1999). "Semiquantitative analysis of Th1 and Th2 cytokine expression in CD3+, CD4+, and CD8+ renal-cell-carcinoma-infiltrating lymphocytes." Cancer Immunol Immunother, vol. 48, No. 4: pp. 204-208.
Emori, Y., H. Sasaki, et al. (1996). "Effect of Z-100, an immunomodulator extracted from human type tubercle bacilli, on the pulmonary metastases of Lewis lung carcinoma in attempt to regulate suppressor T cells and suppressor factor, IL-4." Biotherapy 9(4): 249-56.
Ertl, B., F. Heigl, et al. (2000). "Lectin-mediated bioadhesion: preparation, stability and caco-2 binding of wheat germ agglutinin-functionalized Poly(D,L-lactic-co-glycolic acid)-microspheres." J Drug Targt 8(3): 173-84.
Fan, X. G., W. E. Liu, et al. (1998). "Circulating Th1 and Th2 cytokines in patients with hepatitis C virus infection." Mediators Inflamm 7(4): 295-7.
Finke, J. H., P. Rayman, et al. (1992). "Characterization of a human renal cell carcinoma specific cytotoxic CD8+ T cell line." J Immunother 11(1): 1-11.

(56) References Cited

OTHER PUBLICATIONS

Finke, J. H., P. Rayman, et al. (1994). "Characterization of tumor-infiltrating lymphocyte subsets from human renal cell carcinoma: specific reactivity defined by cytotoxicity, interferon-gamma secretion, and proliferation." J Immunother Emphasis Tumor Immunol 15(2): 91-104.
Flanagan, D. L. et al. (1999). "Th1 Cytokines and NK Cells Participate in the Development of Murine Syngeneic Graft-Versus-Host Disease." The Journal of Immunology, vol. 163, No. 3: pp. 1170-1177.
Fowler, D. H., J. Breglio, et al. (1996). "Allospecific CD4+, Th1/Th2 and CD8+, Tc1/Tc2 populations in murine GVL: type I cells generate GVL and type II cells abrogate GVL." Biol Blood Marrow Transplant 2(3): 118-25.
Fowler, D. H. And R. E. Gress (2000). "Th2 and Tc2 cells in the regulation of GVHD, GVL, and graft rejection: considerations for the allogeneic transplantation therapy of leukemia and lymphoma." Leuk Lymphoma 38(3-4): 221-34.
Frassoni, F., M. Labopin, et al. (1996). "Results of allogeneic bone marrow transplantation for acute leukemia have improved in Europe with time—a report of the acute leukemia working party of the European group for blood and marrow transplantation (EBMT)." Bone Marrow Transplant 17(1): 13-8.
Freeman, G. J. et al. (2002). "Protect the killer: CTLs need defenses against the tumor." Nature Medicine, vol. 8, No. 8: pp. 787-789.
Friess, H., H. G. Beger, et al. (1996). "Treatment of advanced pancreatic cancer with mistletoe: results of a pilot trial." Anticancer Res 16(2): 915-20.
Fujimoto, T. et al. (1997). "Streptococcal Preparation OK-432 is a Potent Inducer of IL-12 and a T Helper Cell 1 Dominant State." The Journal of Immunology, vol. 158, No. 12: pp. 5619-5626.
Fujisao, S. et al. (1998). "Th1/Th2 balance alteration in the clinical course of a patient with pure red cell aplasia and thymoma." British Journal of Haematology, vol. 103, No. 2: pp. 308-310.
Gabrilovich, D. I. et al. (1996). "Dendritic Cells in Antitumor Immune Responses. II. Dendritic Cells Grown from Bone Marrow Precursors, but Not Mature DC from Tumor-Bearing Mice, Are Effective Antigen Carriers in the Therapy of Established Tumors." Cellular Immunology, vol. 170, No. 1: pp. 111-119.
Gale, R. P. et al. (1984). "How Does Bone-Marrow Transplantation Cure Leukaemia?" The Lancet, vol. 2, No. 8393: pp. 28-30.
Garlie, N.K., A.V. LeFever, et al. (1999). "T cells coactivated with immobilized anti-CD3 and anti-CD28 as potential immunotherapy for cancer." J Immunother 22(4): 336-45.
Yashiro-Ohtani, Y. et al. (2000). "Non-CD28 Costimulatory Molecules Present in T Cell Rafts Induce T Cell Costimulation by Enhancing the Association of TCR with Rafts." The Journal of Immunology, vol. 164, No. 3: pp. 1251-1259.
Yoon, T. J. et al. (1998). "Prophylactic effect of Korean mistletoe (Viscum album coloratum) extract on tumor metastasis is mediated by enhancement of NK cell activity." International Journal of Immunopharmacology, Vo. 20, No. 4-5: pp. 163-172.
Zitvogel, L. et al. (1996). "Therapy of Murine Tumors with Tumor Peptide-Pulsed Dendritic Cells: Dependence on T Cells, B7 Costimulation, and T Helper Cell 1-associated Cytokines." Journal of Experimentive Medicine, vol. 183, No. 1: pp. 87-97.
Agrewala et al. "Delivery of antigen in allogeneic cells preferentially generates CD4+Th1 cells", Clinical and Experimental Immunology, 2003, vol. 134, pp. 13-22.
Dinauer et al: "Selective Targeting of Antibody-Conjugated Nanoparticles to Leukemic Cells and Primary T-Lymphocytes", Biomaterials, vol. 26, No. 29, Oct. 2005, pp. 5898-5906.
Encke et al., "Prophylactic and therapeutic vaccination with dendritic cells against hepatitis C virus infection", Clinical and Experimental Immunology, 2005, vol. 142, pp. 362-269.
Fowler et al. "Donor lymphoid cells of TH2 cytokine phenotype reduce lethal graft versus host disease and facilitate fully allogeneic cell transfers in sublethally irradiated mice." Prog Clin Biol Res, 1994, vol. 389, pp. 533-540.
Gong et al., "Fusions of human ovarian carcinoma cells with autologous or allogeneic dendritic cells induce antitumor immunity", The Journal of Immunology, 2000, vol. 165, pp. 1705-1711.
Har-Noy, "Completely mismatched allogeneic CD3/CD28 cross-linked Th1 memor cells elicit anti-leukemia effects in unconditioned hosts without GVHD toxicity", 2008, Leukemia Research, vol. 32, No. 12, pp. 1903-1913.
Meier et al: "Development of a Latex Conjugated Immuno Cytological Marker for Scanning Electron Microscopic Analysis of Quail Chick Chimeras", Journal of Experimental Zoology, vol. 224, No. 1, 1982, pp. 25-38.
Sinha et al.: "Biodegradable Microspheres for Protein Delivery", Journal of Controlled Release, vol. 90, No. 3, Jul. 31, 2003, pp. 261-280.
Raghupathy, R. et al. (1999). "Maternal Th1- and Th2-Type Reactivity to Placental Antigens in Normal Human Pregnancy and Unexplained Recurrent Spontaneous Abortions." Cellular Immunology, vol. 196, No. 2: pp. 122-130.
Rondon, G., S. Giralt, et al. (1996). "Graft-versus-leukemia effect after allogeneic bone marrow transplantation for chronic lymphocytic leukemia." Bone Marrow Transplant 18(3): 669-72.
Rosenberg, S. A. (2001). "Progress in the development of immunotherapy for the treatment of patients with cancer." Journal of Internal Medicine, vol. 250, No. 6: pp. 462-475.
Roussel, E. et al. (1996). "Predominance of a type 2 intratumoural immune response in fresh tumour-infiltrating lymphocytes from human gliomas." Clinical and Experimental Immunology, vol. 105, No. 2: pp. 344-352.
Rubbi, C.P. et al. (1993). "Evidence of surface antigen detachment during incubation of cells with immunomagnetic beads." Journal of Immunology Methods, vol. 166, No. 2: pp. 233-241.
Santin, A. D. et al. (2000). "Interleukin-10 Increases Th1 Cytokine Production and Cytotoxic Potential in Human Papillomavirus-Specific CD8(+) Cytotoxic T Lymphocytes." Journal of Virology, vol. 74, No. 10: pp. 4729-4737.
Sato, M., S. Goto, et al. (1998). "Impaired production of Th1 cytokines and increased frequency of Th2 subsets in PBMC from advanced cancer patients." Anticancer Res 18(5D): 3951-5.
Saxton, M. L. et al. (1997). "Adoptive Transfer of Anti-CD3-Activated CD4+ T Cells Plus Cyclophosphamide and Liposome-Encapsulated Interleukin-2 Cure Murine MC-38 and 3LL Tumors and Establish Tumor-Specific Immunity." Blood, vol. 89, No. 7: pp. 2529-2536.
Shibuya, T.Y. et al. (2000). "Anti-CD3/Anti-CD28 Bead Stimulation Overcomes CD3 Unresponsiveness in Patients With Head and Neck Squamous Cell Carcinoma." Arch Otolaryngol Head Neck Surg, vol. 126, No. 4: 473-479.
Shinomiya, Y., M. Harada, et al. (1995). "Anti-metastatic activity induced by the in vivo activation of purified protein derivative (PPD)-recognizing Th1 type CD4+ T cells." Immunobiology 193(5): 439-55.
Shurin, M. R., L. Lu, et al. (1999). "Th1/Th2 balance in cancer, transplantation and pregnancy." Springer Semin Immunopathol 21(3): 339-59.
Slavin, S. et al. (2001). "Non-myeloablative allogeneic Stem cell transplantation focusing on immunotherapy of life-threatening malignant and non-malignant diseases." Critical Reviews Oncology Hematology, vol. 39, No. 1-2: pp. 25-29.
Slavin, S. et al. (1995). "Allogeneic cell therapy for relapsed leukemia after bone marrow transplantation with donor peripheral blood lymphocytes." Experimental Hematology, vol. 23, No. 14: pp. 1553-1562.
Slavin, S. et al. (1996). "Allogeneic Cell Therapy With Donor Peripheral Blood Cells and Recombinant Human Interleukin-2 to Treat Leukemia Relapse After Allogeneic Bone Marrow Transplantation." Blood, vol. 87, No. 6: pp. 2195-1204.
Slavin, S. et al. (1996). "Allogeneic Cell Therapy: The Treatment of Choice for All Hematologic Malignancies Relapsing Post BMT." Blood, vol. 87, No. 9: pp. 4011-4013.
Slavin, S. et al. (2001). "Nonmyeloablative stem cell transplantation for the treatment of cancer and life-threatening nonmalignant disorders: past accomplishments and future goals." Cancer Chemother Pharmacol, vol. 48, (Suppl 1): pp. S79-S84.

(56) References Cited

OTHER PUBLICATIONS

Slavin, S. et al. (1998). "Immunotherapy in conjunction with autologous and allogeneic blood or marrow transplantation in lymphoma." Annals of Oncology, vol. 9 (Suppl 1): pp. S31-S39.
Smith, D. R., S. L. Kunkel, et al. (1994). "Production of interleukin-10 by human bronchogenic carcinoma." Am J Pathol 145(1): 18-25.
Smyth, M. J. et al. (2002). "New Aspects of Natural-Killer-Cell Surveillance and Therapy of Cancer." Nature Reviews Cancer, vol. 2, No. 11: pp. 850-861.
Sredni, B. et al. (1995). "Bone Marrow-Sparing and Prevention of Alopecia by AS101 in Non-Small-Cell Lung Cancer Patients Treated with Carboplatin and Etoposide." Journal of Clinical Oncology, vol. 13, No. 9: pp. 2342-2353.
Sredni, B. et al. (1996). "Predominance of TH1 Response in Tumor-Bearing Mice and Cancer Patients Treated with AS101." National Journal of Cancer Institute, vol. 88, No. 18: pp. 1276-1284.
Sredni, B., R. H. Xu, et al. (1996). "The protective role of the immunomodulator AS101 against chemotherapy-induced alopecia studies on human and animal models." Int J Cancer 65(1): 97-103.
Stein, G., W. Henn, et al. (1998). "Modulation of the cellular and humoral immune responses of tumor patients by mistletoe therapy." Eur J Med Res 3(4): 194-202.
Stern, B. V. et al. (2002). "Vaccination with Tumor Peptide in CpG Adjuvant Protects Via IFN-Gamma-Dependent CD4 Cell Immunity." The Journal of Immunology, vol. 168, No. 12: pp. 6099-6105.
Tabata, T. et al. (1999). "Th2 Subset Dominance Among Peripheral Blood T Lymphocytes in Patients with Digestive Cancers." American Journal of Surgery, vol. 177, No. 3: pp. 203-208.
Taga, K. et al. (1993). "Human Interleukin-10 Can Directly Inhibit T-Cell Growth." Blood, vol. 81, No. 11: pp. 2964-2971.
Takeuchi, T. et al. (1997). "Th2-like response and antitumor effect of anti-interleukin-4 mAb in mice bearing renal cell carcinoma." Cancer Immunol Immunother, vol. 43, No. 6: pp. 375-381.
Tanaka, K., K. Kemmotsu, et al. (1998). "[Flow cytometric analysis of helper T cell subsets (Th1 and Th2) in healthy adults]." Rinsho Byori 46(12): 1247-51.
Tanaka, J., M. Imamura, et al. (1997). "The important balance between cytokines derived from type 1 and type 2 helper T cells in the control of graft-versus-host disease." Bone Marrow Transplant 19(6): 571-6.
Tatsumi, T. et al. (2002). "Disease-associated bias in T helper type 1 (Th1)/Th2 CD4(+) T cell responses against MAGE-6 in HLA-DRB10401(+) patients with renal cell carcinoma or melanoma." Journal of Experimental Medicine, vol. 196, No. 5: pp. 619-628.
Terao, H., M. Harada, et al. (1994). "Th1 type CD4+ T cells may be a potent effector against poorly immunogenic syngeneic tumors." Biotherapy 8(2): 143-51.
Tessmar, J. et al. (2003). "The use of poly(ethylene glycol)-block-poly(lactic acid) derived copolymers for the rapid creation of biomimetic surfaces." Biomaterials, vol. 24, No. 24: pp. 4475-4486.
Thanhauser, A., A. Bohle, et al. (1995). "The induction of bacillus-Calmette-Guerin-activated killer cells requires the presence of monocytes and T-helper type-1 cells." Cancer Immunol Immunother 40(2): 103-8.
Thomas, A. K. et al. (2002). "A Cell-Based Artificial Antigen-Presenting Cell Coated with Anti-CD3 and CD28 Antibodies Enables Rapid Expansion and Long-Term Growth of CD4 T Lymphocytes." Clinical Immunology, vol. 105, No. 3: pp. 259-272.
Thomas, E., R. Storb, et al. (1975). "Bone-marrow transplantation (first of two parts)." N Engl J Med 292(16): 832-43.
Thomas, E. D., R. Storb, et al. (1975). "Bone-marrow transplantation (second of two parts)." N Engl J Med 292(17): 895-902.
Tilg, H. et al. (1994). "Interleukin-6 (IL-6) as an Anti-inflammatory Cytokine: Induction of Circulating IL-1 Receptor Antagonist and Soluble Tumor Necrosis Factor Receptor p55." Blood, vol. 83, No. 1: pp. 113-118.
To, W. C. et al. (2000). "Therapeutic Efficacy of Th1 and Th2 L-selectin—CD4+ Tumor-Reactive T Cells." Laryngoscope vol. 110, (10 Pt 1): pp. 1648-1654.
Ueno, N. T., G. Rondon, et al. (1998). "Allogeneic peripheral-blood progenitor-cell transplantation for poor-risk patients with metastatic breast cancer." J Clin Oncol 16(3): 986-93.
van Besien, K., P. Thall, et al. (1997). "Allogeneic transplantation for recurrent or refractory non-Hodgkin's lymphoma with poor prognostic features after conditioning with thiotepa, busulfan, and cyclophosphamide: experience in 44 consecutive patients." Biol Blood Marrow Transplant 3(3): 150-6.
Voutsadakis, I. A. (2003). "NK cells in allogeneic bone marrow transplantation." Cancer Immunol Immunother, vol. 52, No. 9: pp. 525-534.
Vowels, B. R. et al. (1994). "Th2 Cytokine mRNA Expression in Skin in Cutaneous T-Cell Lymphoma." The Journal of Investigative Dermatology, vol. 103, No. 5: pp. 669-673.
Wang, Q. et al. (1995). "Selective Cytokine Gene Expression in Renal Cell Carcinoma Tumor Cells and Tumor-Infiltrating Lymphocytes." International Journal of Cancer, vol. 61, No. 6: pp. 780-785.
Weber, K., U. Mengs, et al. (1998). "Effects of a standardized mistletoe preparation on metastatic B16 melanoma colonization in murine lungs." Arzneimittelforschung 48(5): 497-502.
Weiden, P. L. et al. (1981). "Antileukemic Effect of Chronic Graft-Versus-Host Disease: Contribution to Improved Survival After Allogeneic Marrow Transplantation." New England Journal of Medicine, vol. 304 No. 25: pp. 1529-1533.
Whitmore, M. et al. (1999). "LPD lipopolyplex initiates a potent cytokine response and inhibits tumor growth." Gene Therapy, vol. 6, No. 11: pp. 1867-1875.
Wong, B. R. et al. (1999). "TRANCE is a TNF family member that regulates dendritic cell and osteoclast function." Journal of Leukocyte Biology, vol. 65, No. 6: pp. 715-724.
Woo, E. Y. et al. (2001). "Regulatory CD4(+)CD25(+) T Cells in Tumors from Patients with Early-Stage Non-Small Cell Lung Cancer and Late-Stage Ovarian Cancer." Cancer Research, vol. 61, No. 12: pp. 4766-4772.
Woo, E. Y. et al. (2002). "Cutting edge: Regulatory T Cells from Lung Cancer Patients Directly Inhibit Autologous T cell proliferation." J Immunol 168(9): 4272-6.
Yamamura, M. (1992). "Defining protective responses to pathogens: cytokine profiles in leprosy lesions." Science 255 (5040): 12.
Office Action for Japanese Patent Application No. 2014-509383, dated Feb. 24, 2015.
Shu, Uno, et al., "Activated T cells induce interleukin-12 production by monocytes via CD40-CD40 ligand interaction," European Journal of Immunology, 25.4 (1995): 1125-1128.
Examination Report issued in related Taiwanese patent application No. 101136820, dated Jan. 6, 2016.
V.A. Musatov, M.I. Kozlov, Introduction to transplantology, Study guide for the students of the medical higher educational institution, Novosibirsk State University, Institute of Clinical Immunology, Siberian Branch of the Russian Academy of Medical Sciences, 2000, Chapter II; with machine translation.
Substantive Examination Report issued in related application PH 1-2013-502253, dated May 16, 2017.
Examination Report issued for related Indian patent application No. 8576/CHENP/2013, dated Jul. 6, 2018.
Hubel et al. (2005), "Effective storage of granulocytes collected by centrifugation leukapheresis from donors stimulated with granulocyte-colony-stimulating factor", Transfusion, vol. 45, No. 12, pp. 1876-1889.
Parkins et al. (2006), "Overnight storage of autologous stem cell apheresis products before cryopreservation does not adversely impact early or long-term engraftment following transplantation", Bone Marrow Transplantation, vol. 38, No. 9, pp. 609-614.
Extended European Search Report for EP12779413.9, dated Oct. 16, 2014.
Written Opinion for Singapore Patent Application No. 2013081617, dated Dec. 8, 2014.
Geppert, T.D. et al. (1988). "Activation of T Lymphocytes by Immobilized Monoclonal Antibodies to CD3, Regulatory Influences of Monoclonal Antibodies to Additional T Cell Surface Determinants." J. Clin. Invest., vol. 81: pp. 1497-1505.

(56) References Cited

OTHER PUBLICATIONS

Ghosh, P., K. L. Komschlies, et al. (1995). "Gradual loss of T-helper 1 populations in spleen of mice during progressive tumor growth." J Natl Cancer Inst 87(19): 1478-83.

Gorelik, L., A. Prokhorova, et al. (1994). "Low-dose melphalan-induced shift in the production of a Th2-type cytokine to a Th1-type cytokine in mice bearing a large MOPC-315 tumor." Cancer Immunol Immunother 39(2): 117-26.

Grakoui, A. et al. (1999). "The Immunological Synapse: A Molecular Machine Controlling T Cell Activation." Science, vol. 285, No. 5425: pp. 221-227.

Granucci, F. et al. (2001). "Transcriptional reprogramming of dendritic cells by differentiation stimuli." Eur J Immunol, vol. 31, No. 9: pp. 2539-2546.

Grigg, A., P. Bardy, et al. (1999). "Fludarabine-based non-myeloablative chemotherapy followed by infusion of HLA-identical stem cells for relapsed leukaemia and lymphoma." Bone Marrow Transplant 23(2): 107-10.

Grohmann, U., M. C. Fioretti, et al. (1998). "Dendritic cells, interleukin 12, and CD4+ lymphocytes in the initiation of class I-restricted reactivity to a tumor/self peptide." Crit Rev Immunol 18(1-2): 87-98.

Hara, I., H. Hotta, et al. (1996). "Rejection of mouse renal cell carcinoma elicited by local secretion of interleukin-2." Jpn J Cancer Res 87(7): 724-9.

Heine, G. et al. (2002). "A shift in the Th(1)/Th(2) ratio accompanies the clinical remission of systemic lupus erythematosus in patients with end-stage renal disease." Nephrology Dialysis Transplantion, vol. 17, No. 10: pp. 1790-1794.

Heniford, B. T. et al. (1994). "Interleukin-8 Suppresses the Toxicity and Antitumor Effect of Interleukin-2." Journal of Surgical Research, vol. 56, No. 1: pp. 82-88.

Herlyn, D. and B. Birebent (1999). "Advances in cancer vaccine development." Ann Med 31(1): 66-78.

Horiguchi, S. et al. (1999). "Primary Chemically Induced Tumors Induce Profound Immunosuppression Concomitant with Apoptosis and Alterations in Signal Transduction in T Cells and NK Cells." Cancer Research, vol. 59, No. 12: pp. 2950-2956.

Inagawa, H., T. Nishizawa, et al. (1998). "Mechanisms by which chemotherapeutic agents augment the antitumor effects of tumor necrosis factor: involvement of the pattern shift of cytokines from Th2 to Th1 in tumor lesions." Anticancer Res 18(5D): 3957-64.

Ito, N. et al. (1999). "Lung Carcinoma: Analysis of T Helper Type 1 and 2 Cells and T Cytotoxic Type 1 and 2 Cells by Intracellular Cytokine Detection with Flow Cytometry." Cancer, vol. 85, No. 11: pp. 2359-2367.

Janes, P. W. et al. (1999). "Aggregation of Lipid Rafts Accompanies Signaling Via the T Cell Antigen Receptor." The Journal of Cell Biology, vol. 147, No. 2: pp. 447-461.

Jung, U. et al. (Nov. 2003). "CD3/CD28-costimulated T1 and T2 subsets: differential in vivo allosensitization generates distinct GVT and GVHD effects." Blood, vol. 1, No. 9: pp. 3439-3446.

Kadowaki, N. et al. (2002). "Natural Type I Interferon-Producing Cells as a Link Between Innate and Adaptive Immunity." Human Immunology, vol. 63, No. 12: pp. 1126-1132.

Kai, S. and H. Hara (2003). "Allogeneic hematopoietic stem cell transplantation." Therap Apher Dial 7(3): 285-91.

Kasakura, S. (1998). "[A role for T-helper type 1 and type 2 cytokines in the pathogenesis of various human diseases]." Rinsho Byori 46(9): 915-21.

Kitahara, S., M. Ikeda, et al. (1996). "Inhibition of head and neck metastatic and/or recurrent cancer by local administration of multi-cytokine inducer OK-432." J Laryngol Otol 110(5): 449-53.

Knoefel, B., K. Nuske, et al. (1997). "Renal cell carcinomas produce IL-6, IL-10, IL-11, and TGF-beta 1 in primary cultures and modulate T lymphocyte blast transformation." J Interferon Cytokine Res 17(2): 95-102.

Kobayashi, M. et al. (1998). "A Pathogenic Role of Th2 Cells and Their Cytokine Products on the Pulmonary Metastasis of Murine B16 Melanoma." The Journal of Immunology, vol. 160, No. 12: pp. 5869-5873.

Kobayashi, M., R. B. Pollard, et al. (1997). "Inhibition of pulmonary metastasis by Z-100, an immunomodulatory lipid-arabinomannan extracted from Mycobacterium tuberculosis, in mice inoculated with B16 melanoma." Anticancer Drugs 8(2): 156-63.

Lahn, M. et al. (1999). "Pro-Inflammatory and T Cell Inhibitory Cytokines are Secreted at High Levels in Tumor Cell Cultures of Human Renal Cell Carcinoma." European Urology, vol. 35, No. 1: pp. 70-80.

Langenkamp, A. et al. (2000). "Kinetics of dendritic cell activation: impact on priming of TH1, TH2 and nonpolarized T cells." Nature Immunology, vol. 1, No. 4: 311-316.

Laux, I. et al. (2000). "Response Differences between Human CD4(+) and CD8(+) T-Cells during CD28 Costimulation: Implications for Immune Cell-Based Therapies and Studies Related to the Expansion of Double-Positive T-Cells during Aging." Clinical Immunology, vol. 96, No. 3: pp. 187-197.

Le Bon, A. et al. (2002). "Links between innate and adaptive immunity via type I interferon," Current Opinion Immunology, vol. 14, No. 4: pp. 432-436.

Lee, P. P. et al. (1997). "T Helper 2-Dominant Antilymphoma Immune Response is Associated With Fatal Outcome." Blood, vol. 90, No. 4: pp. 1611-1617.

Levine, B.L. et al. (1997). "Effects of CD28 Costimulation on Long-Term Proliferation of CD4+ T Cells in the Absence of Exogenous Feeder Cells." The Journal of Immunology, vol. 159, No. 12: pp. 5921-5930.

Li, L. et al. (1998), "Cyclophosphamide Given After Active Specific Immunization Augments Antitumor Immunity by Modulation of Th1 Commitment of CD4+ T Cells." Journal of Surgical Oncology, vol. 67, No. 4: pp. 221-227.

Liebowitz, D.N. et al. (1998). "Costimulatory approaches to adoptive immunotherapy." Current Opinion Oncology, vol. 10, No. 6: pp. 533-541.

Lowes, M. A., G. A. Bishop, et al. (1997). "T helper 1 cytokine mRNA is increased in spontaneously regressing primary melanomas." J Invest Dermatol 108(6): 914-9.

Ludviksson, B. R. et al. (2000). "The effect of TGF-β1 on immune responses of naive versus memory CD4+ Th1/Th2 T cells." Eur J Immunol, vol. 30, No. 7: pp. 2101-2111.

Lum, L.G. et al (2001). "Immune modulation in cancer patients after adoptive transfer of ani-CD3/anti-CD28-costimulated T-cells—phase I clinical trial." Journal of Immunotherapy, vol. 24, No. 5: pp. 408-419.

Ma, J. et al. (1998). "Use of encapsulated single chain antibodies for induction of anti-idiotypic humoral and cellular immune responses." Journal of Pharmaceutical Sciences, Vo. 87, No. 11: pp. 1375-1378.

Maeurer, M. J., D. M. Martin, et al. (1995). "Host immune response in renal cell cancer: interleukin-4 (IL-4) and IL-10 mRNA are frequently detected in freshly collected tumor-infiltrating lymphocytes." Cancer Immunol Immunother 41(2): 111-21.

Maus, M. V. et al. (2002). "Ex vivo expansion of polyclonal and antigen-specific cytotoxic T lymphocytes by artificial APCs expressing ligands for the T-cell receptor, CD28 and 4-1BB." Nature Biotechnology, vol. 20, No. 2: pp. 143-148.

Menetrier-Caux, C. et al. (1999). "Renal cell carcinoma induces interleukin 10 and prostaglandin E2 production by monocytes." British Journal of Cancer, vol. 79, No. 1: pp. 119-130.

Moran, M. et al. (1998). "Engagement of GPI-Linked CD48 Contributes to TCR Signals and Cytoskeletal Reorganization: A Role for Lipid Rafts in T Cell Activation." Immunity, vol. 9, No. 6: pp. 787-796.

Muller, M. et al. (2003). "Surface modification of PLGA microspheres." Journal of Biomedic Material Research, vol. 66A, No. 1: pp. 55-61.

Nabioullin, R. et al. (1994). "Interleukin-10 is a potent inhibitor of tumor cytotoxicity by human monocytes and alveolar macrophages." Journal of Leukocyte Biology, vol. 55, No. 4: pp. 437-442.

Nakagomi, H. et al. (1995). "Lack of Interleukin-2 (IL-2) Expression and Selective Expression of IL-10 mRNA in Human Renal Cell Carcinoma." Int. Journal of Cancer, vol. 63, No. 3: pp. 366-371.

(56) References Cited

OTHER PUBLICATIONS

Nishimura, T. et at. (2000). "The critical role of Th1-dominant immunity in tumor immunology." Cancer Chemother Pharmacol, vol. 46 (Suppl): S52-S61.

Nitta, T., M. Hishii, et al. (1994). "Selective expression of interleukin-10 gene within glioblastoma multiforme." Brain Res 649(1-2): 122-8.

O'Donnell P.B. et al. (1997). "Preparation of microspheres by the solvent evaporation technique." Advanced Drug Delivery Reviews, vol. 28, No. 1: pp. 25-42.

Oka, H. et al. (1999). "An immunomodulatory arabinomannan extracted from Mycobacterium tuberculosis, Z-100, restores the balance of Th1/Th2 cell responses in tumor bearing mice," Immunology Letters, vol. 70, No. 2: pp. 109-117.

Okamoto, T. et al. (1997). "Local Injection of OK432 Can Augment the TH1-Type T-Cell Response in Tumor-Draining Lymph Node Cells and Increase Their Immunotherapeutical Potential." International Journal of Cancer, vol. 70, No. 5: pp. 598-605.

Okutomi, T., Y. Kato, et al. (2000). "[Clinical effects of adjuvant therapy using Z-100 (Ancer 20 injection) for oral cancer—prevention of stomatitis and hematopoietic impairment]." Gan to Kagaku Ryoho 27(1): 65-71.

Onishi, T. et al. (1999). "An assessment of the immunological environment based on intratumoral cytokine production in renal cell carcinoma." BJU International, vol. 83, No. 4: pp. 488-492.

Raghupathy, R. (1997). "Th1-type immunity is incompatible with successful pregnancy." Immunology Today, vol. 18, No. 10: pp. 478-482.

Daniel M. R., (1976). "Factors Influencing the Survival of Cell Monolayers During Storage at 4". Br. J. exp. Path. 57, pp. 137, 140, 142, 145.

International Search Report and Written Opinion; PCT/US2012/036103; dated Oct. 18, 2012.

\* cited by examiner

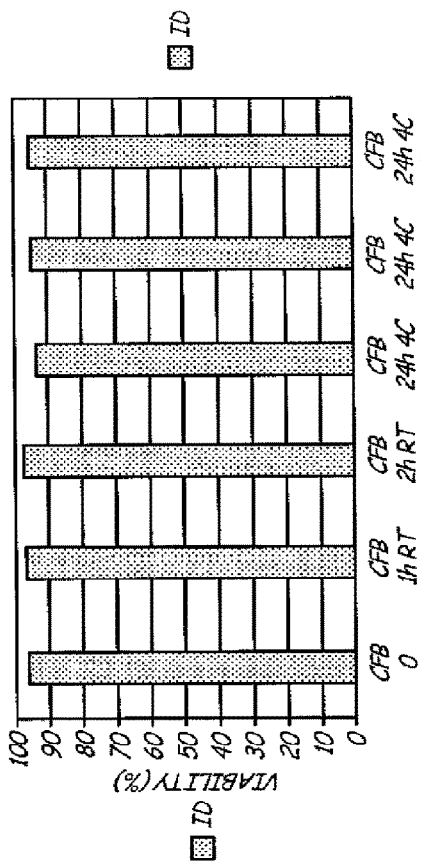
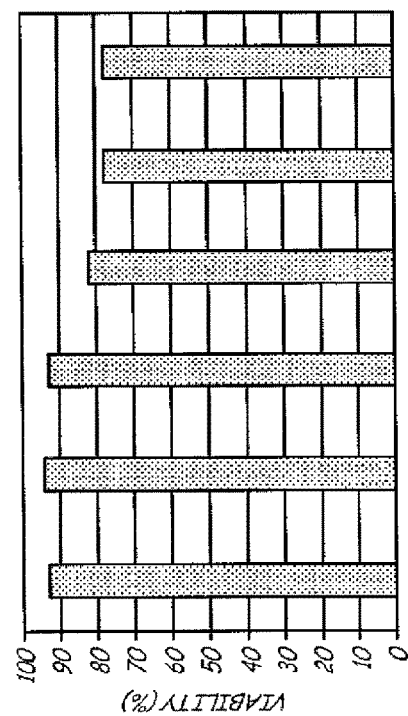
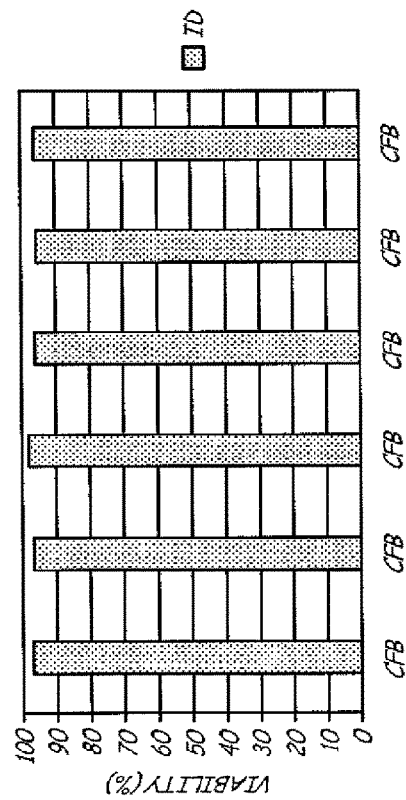
Fig. 3A
Fig. 3B
Fig. 3C

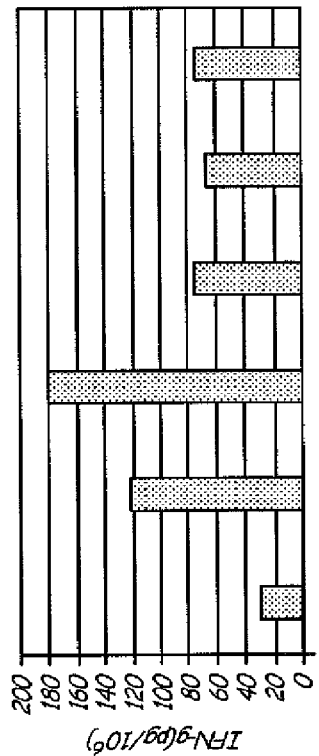
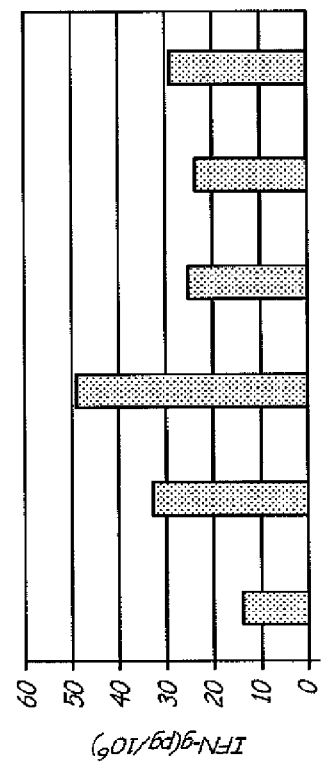
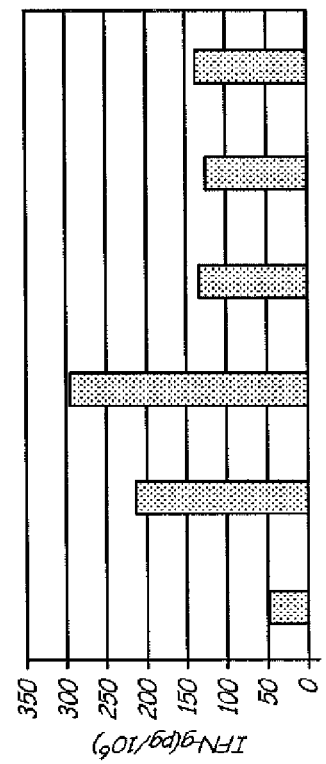
Fig. 4A
Fig. 4B
Fig. 4C

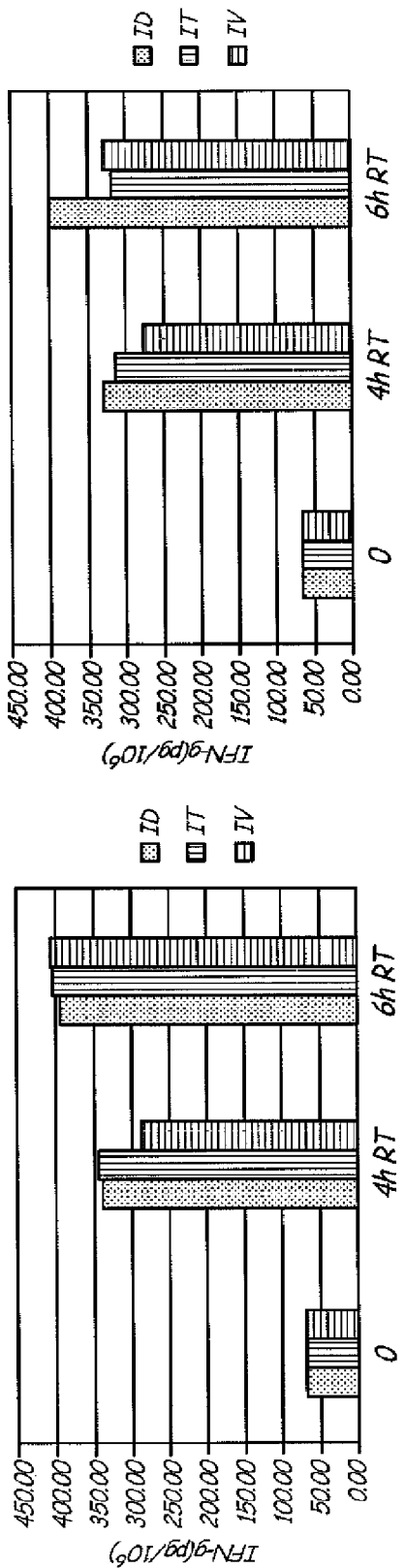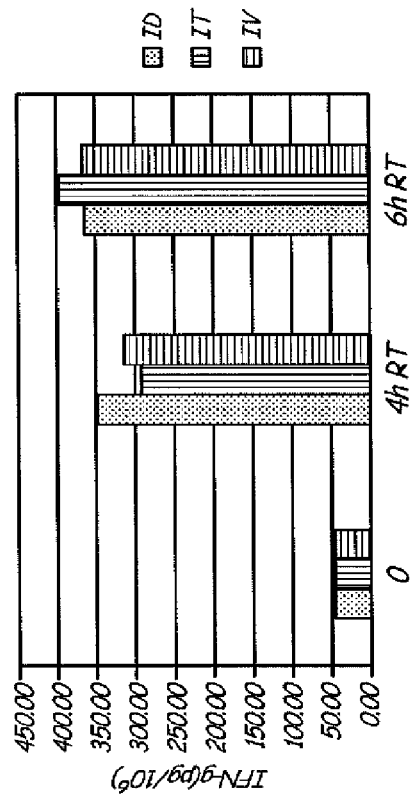
Fig. 8A  Fig. 8B  Fig. 8C

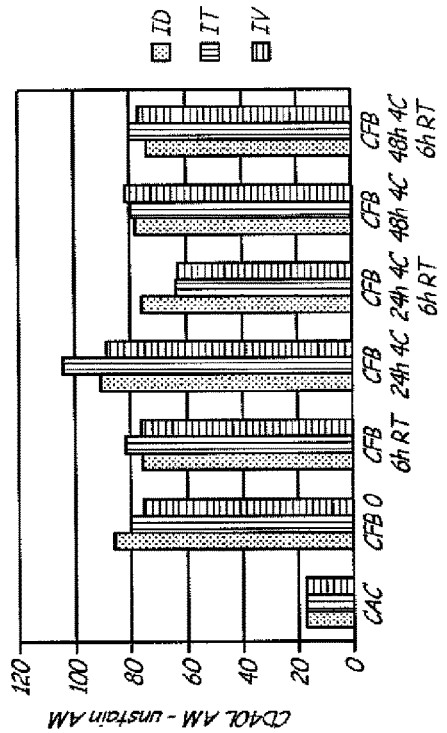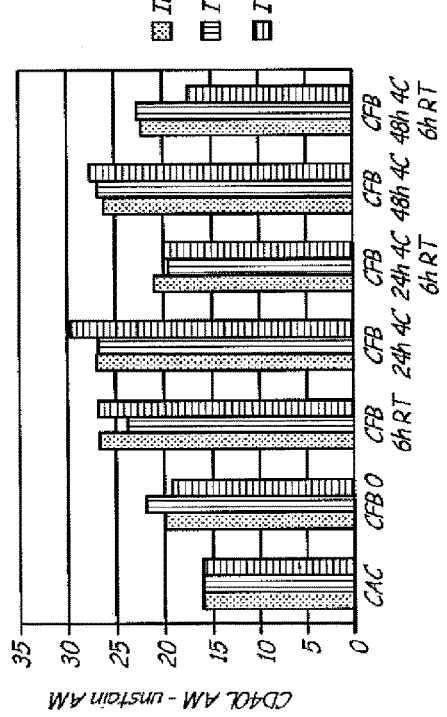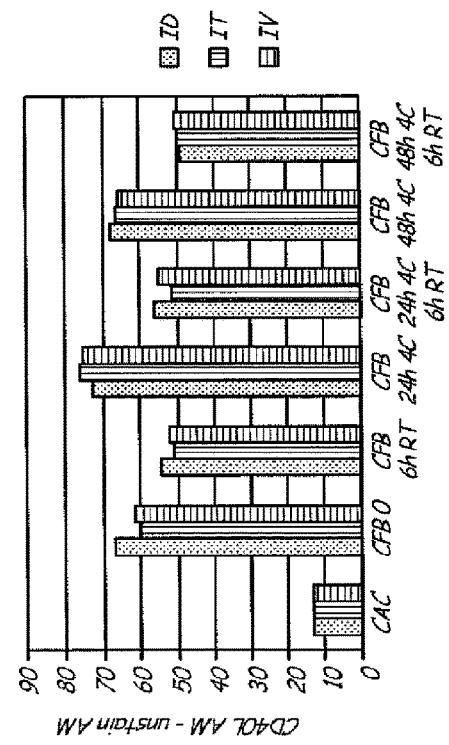

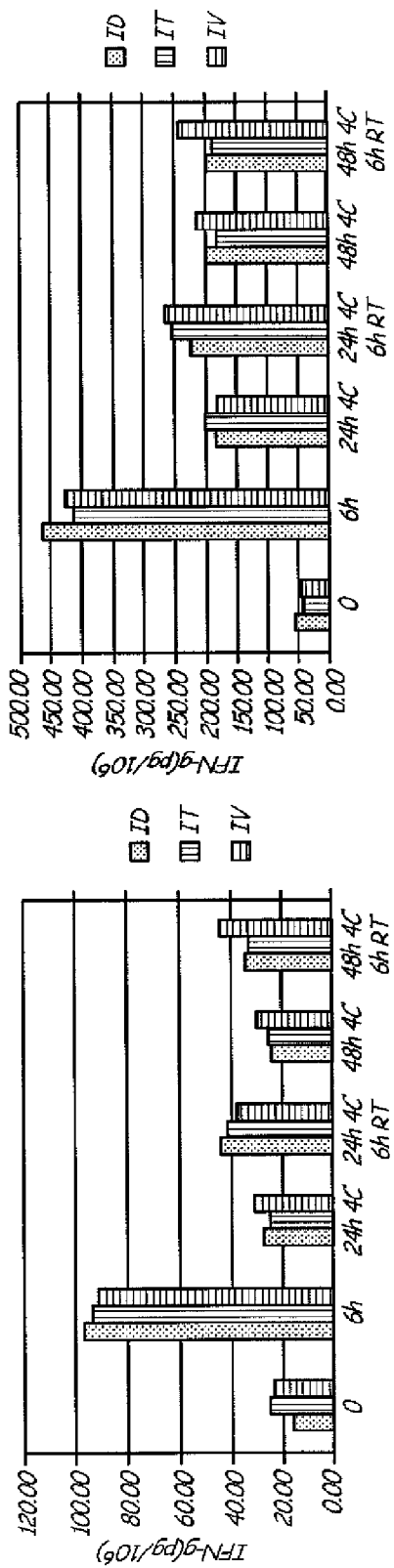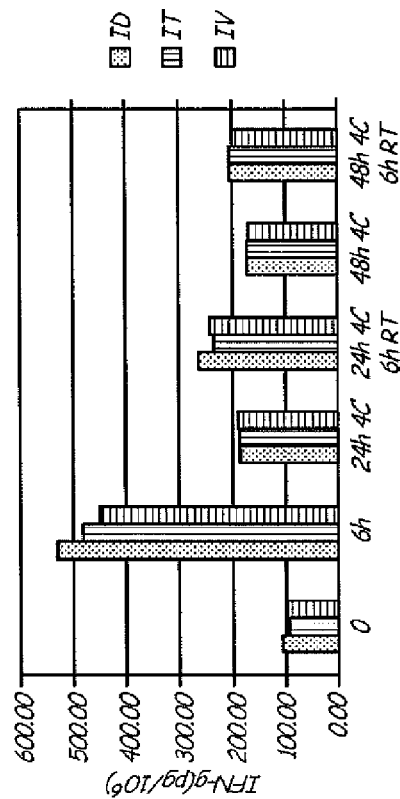

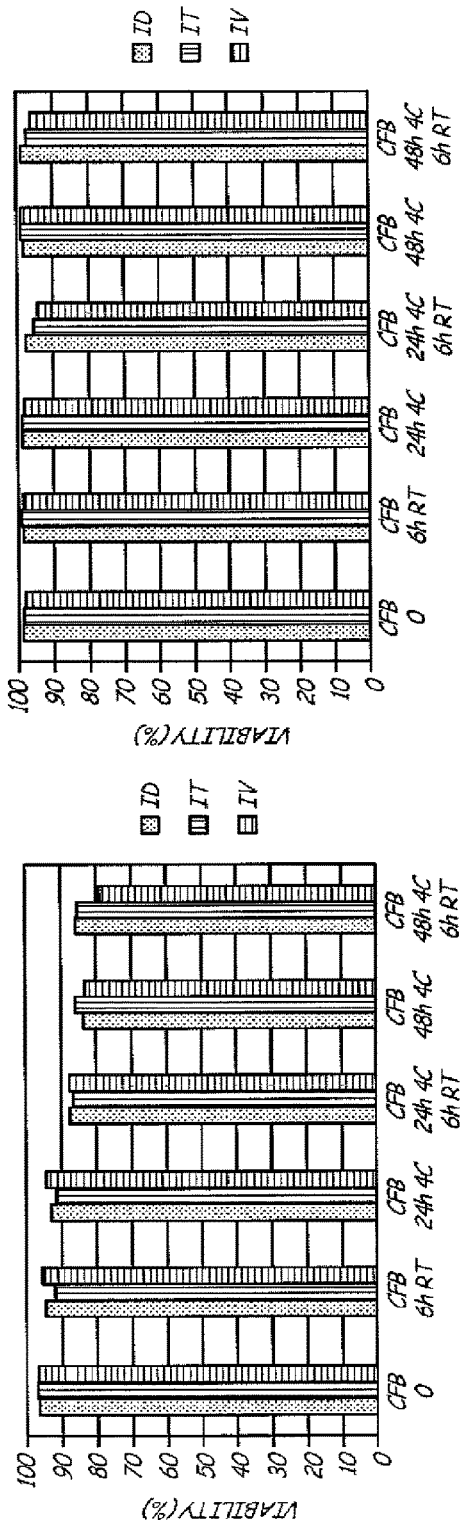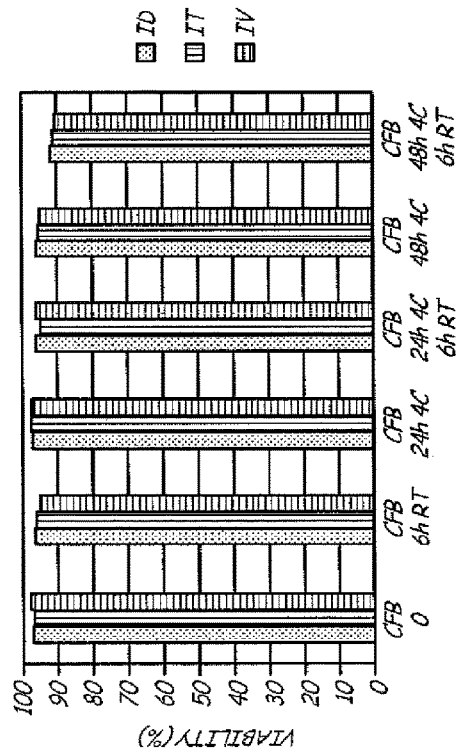

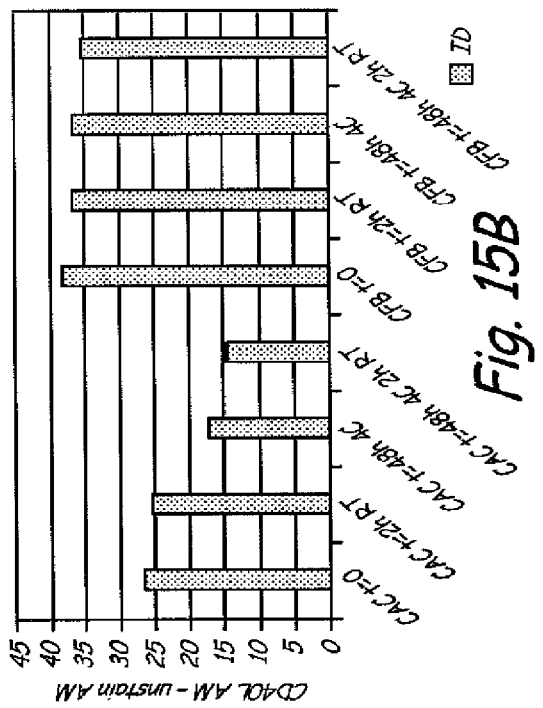
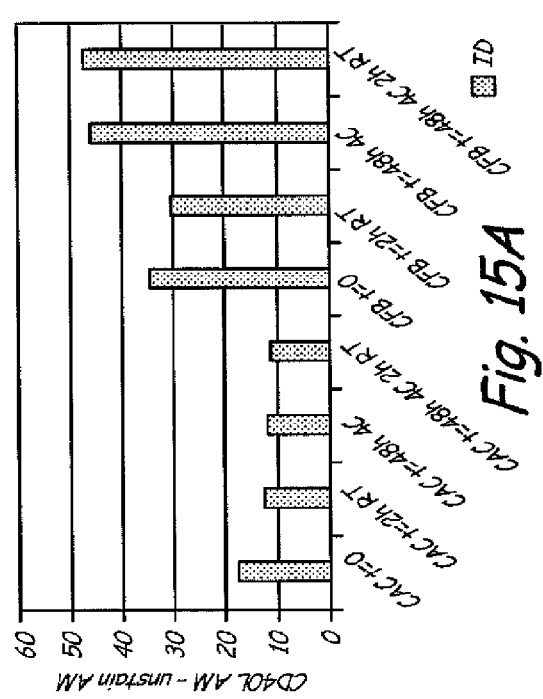
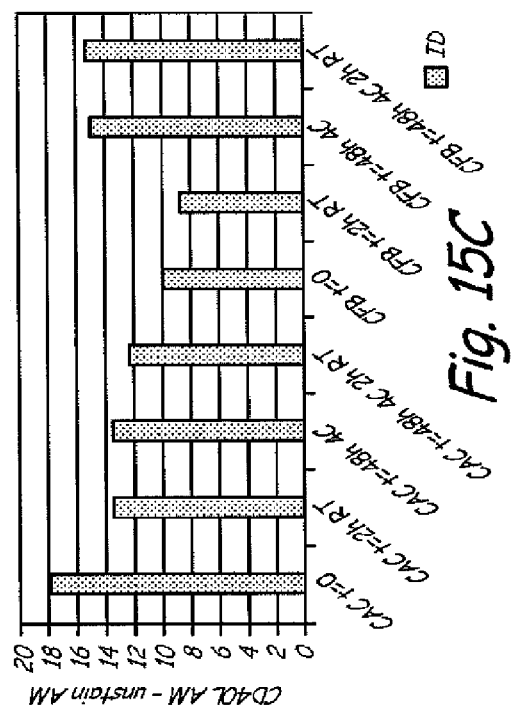
Fig. 15A
Fig. 15B
Fig. 15C

METHODS FOR HANDLING BIOLOGICAL DRUGS CONTAINING LIVING CELLS

CROSS-REFERENCE TO RELATED APPLICATION

This Application is a Section 371 National Stage Application of International Application No. PCT/US2012/036103, filed May 2, 2012, in English, which claims priority to U.S. provisional patent application Ser. No. 61/481,991, filed May 3, 2011, U.S. provisional patent application Ser. No. 61/528,493, filed Aug. 29, 2011, U.S. provisional patent application Ser. No. 61/565,225, filed Nov. 30, 2011, U.S. provisional patent application Ser. No. 61/582,878, Filed Jan. 4, 2012, the contents of which are hereby incorporated by reference in their entirety.

FIELD

This invention relates to methods for handling biological drugs containing live cell suspensions formulated in non-nutritive buffer. More specifically, the present invention relates to the packaging, shipping, and distribution of live immune cell suspensions in non-nutritive media, whereby the cells maintain their unique identity, function and viability properties.

BACKGROUND

Cell therapy is a potentially curative therapy against tumors, viruses and bacterial pathogens. Cell therapy can also be used to treat autoimmune diseases (e.g. rheumatoid arthritis, multiple sclerosis and type I diabetes), neurological disorders (such as Alzheimer's, ALS and Parkinson's disease), as well as anti-aging treatment, wound healing and treatment of cardiovascular disorders. Harnessing the power of the immune system to treat or prevent diseases is a major goal of immunotherapy. A variety of immunotherapy methods and compositions have been developed in order to enhance or suppress the immune response in patients. Cell therapy methods often involve ex-vivo manipulations such as proliferation, differentiation and/or activation of cells. Cells that are more than minimally manipulated are considered to be biological drugs by the United States Food and Drug Administration (USFDA) as well as regulatory agencies in other jurisdictions. Before such biological drugs can be marketed for treatment or prevention of any disease, these products must first be investigated in human clinical trials under an Investigational New Drug Application (IND) or equivalent.

For commercial use, the processes used to manufacture biological drugs containing living cells must be standardized so that the resulting cells have pre-determined identity, functional and viability release criteria. The processes to cause the proliferation, differentiation and/or activation of cells intended for use as a biological drug generally occurs ex-vivo where the cells are kept in nutrient-rich culture media. However, prior to administering the cells to humans, the cells must be transferred to a non-nutrient infusion buffer. Because these buffer solutions do not contain nutrients, the cells remain viable for only short periods of time. Further, even if the cells remain viable after being placed in non-nutrient infusion buffer, they quickly lose their unique identity and functional characteristics. Losing their unique identity and functional characteristics disqualifies the cells to be used as a biological drug. This limitation requires that cells intended for use of biological drugs must be formulated at or near the point-of-care. The requirement that cells be formulated at or near the point-of-care because of the limited shelf life of living cell products in formulation severely limits the commercial viability of this class of product.

Living cells are relatively stable in nutrient rich culture media. Examples of nutrient-rich culture media include, for example, X-Vivol 5 (BioWhittaker, Walkersville, Md.), RPMI 1640, DMEM, Ham's F12, McCoys 7A and Medium 199. The medium can be supplemented with additional ingredients including serum, serum proteins, growth suppressing, and growth promoting substances, such as mitogenic monoclonal antibodies and selective agents for selecting genetically engineered or modified cells. However, transfer of the cells to non-nutritive buffer such as is required for administration to a patient can lead to rapid degradation of the cellular identity, cell viability and the functional characteristics of the cells. Examples of non-nutrient buffers include, for example, isotonic solutions such as normal saline, phosphate buffered saline, 5% dextrose, Plasma-Lyte (Baxter Scientific, Deerfield, Ill.) and Normasol (Abbott Laboratories, Abbott Park, Ill.). In addition, when cells are transferred to non-nutritive buffer, it is generally believed that reagents that provide activation and/or differentiation signals as well as other components such as stimulatory molecules or cytokines should be removed prior to transfer into non-nutritive buffer. (See U.S. Pat. No. 6,867,041 to Berenson et al.) Therefore, cells in non-nutritive buffer generally have a limited shelf-life and can, for example, start losing their identifying properties and activity within minutes and rarely maintain their functional and identity characteristics for more than a few hours.

Currently, immunotherapeutic compositions that include living cells are generally produced in a cGMP facility close to the point of care of the patient (See US patent Publication no. 2003/0175242 to Gruenberg). Formulation of biological drugs with living cells must be performed under highly controlled and sterile conditions in cGMP facilities. The live cells are manipulated at the cGMP facility and formulated for infusion into a patient. Once the cells are prepared for infusion, the cells are quickly transferred to the point of care site and administered to the patient. The major drawback of this process is that cGMP facilities need to be present near every point of care site. The cGMP facilities require considerable monetary capital to staff and run under the required rules and regulations. The need to establish a multiplicity of these centers at or near every point of care is cost prohibitive and a severe limitation to the commercial potential of this class of drug. This leads to a difficult choice of incurring great expense by building a large number of cGMP facilities in order to increase accessibility to patients or to providing limited accessibility for patients by building only a limited number of cGMP facilities to minimize the capital expenditures. Thus, there is a need in the field of live cell therapeutics for methods that enable cells in non-nutritive buffer to have a more extended shelf-life. Furthermore, a method is needed that would enable the packaging, shipping and mass distribution of formulated cell products suspended in non-nutrient containing infusion buffer.

Problems with maintaining the identity and function of cells used in adoptive immunotherapy after formulation are described, for example, in U.S. Patent Publication No. 2003/0175272 to Gruenberg. This publication teaches that T-cells must be reactivated just prior to patient administration (no more than 4 hours prior to infusion) to maintain functional characteristics of cytokine production. The function of the cells can be maintained up to 48 hours only if the formulation includes autologous plasma. However, collection of plasma from every intended patient is not conducive to mass distribution and commercialization.

SUMMARY

In a first aspect, this invention includes a biologic drug composition. The drug composition comprises living cells formulated in non-nutritive buffer. The living cells, after being stored for greater than about 6 hours in the non-nutritive buffer, maintain their identity and at least one functional characteristic that defined the living cells prior to formulation in the non-nutritive buffer. These living cells are useful in immunotherapy after storage in the non-nutritive buffer. They maintain their identity and at least one functional characteristic that defined the living cells prior to formulation in the non-nutrient buffer for at least 72 hours.

In another aspect, this invention includes a method of handling a biological drug composition with living cells. The method comprises formulating the living cells in a non-nutritive buffer and maintaining the living cells in the non-nutritive buffer at a storage temperature below about 20° C. The living cells maintain their identity and at least one of the functional characteristics of the cells that defined the living cells prior to formulation in the non-nutritive buffer. The living cells are useful for immunotherapy after being stored for greater than about 72 hours in the non-nutritive buffer. Preferably, the storage temperature is in a range between about 4° C. and about 8° C. and the concentration of the cells in the non-nutritive buffer is about $10^7$ cells/ml or greater. In compositions of T-cells, the living cells are preferably formulated in an activated state. In order to activate the T-cells, it is preferable to use immobilized monoclonal antibodies reactive to cell surface molecules. Preferably, the cell surface molecules are a combination of first one of the following: CD3, MHCI, MHCII, CD2 and second a co-stimulatory molecule. Preferably the co-stimulatory molecule is CD28. The living cells are placed in a flexible container or syringe, wherein the flexible container or syringe is packaged in a temperature controlled device that maintains the living cells at the storage temperature. The method also includes shipping and distributing the package in the temperature controlled device to the point of care.

In yet another aspect, this invention includes a method of providing living cell compositions to a point of care facility. The method comprises formulating the living cells in a non-nutritive buffer at a processing facility and transporting the cells to a point of care facility in a package equipped to maintain a storage temperature below about 20° C. The living cells are at the storage temperature for up to about 72 hours while maintaining their identity and at least one of the functional characteristics of the living cells useful in immunotherapy.

In a further aspect, this invention includes a method of administering immunotherapy to a patient. The method comprises administering a composition that includes living cells formulated in non-nutritive buffer, wherein the composition has been stored for up to about 72 hours in the non-nutritive buffer, wherein the living cells maintain their identity and at least one of the functional characteristics of the cells that defined the living cells prior to formulation in the non-nutritive buffer, the living cells useful in immunotherapy.

In yet a further aspect, this invention includes another method of administering immunotherapy to a patient. The method comprises administering a composition that includes living cells formulated in non-nutritive buffer, wherein the composition was previously stored in a frozen state, for example in liquid nitrogen, for up to 2 years or more and has been thawed and formulated and then stored for up to about 72 hours in the non-nutritive buffer, wherein the living cells maintain their identity and at least one of the functional characteristics of the cells that defined the living cells prior to formulation in the non-nutritive buffer, the living cells useful in immunotherapy.

BRIEF DESCRIPTION OF THE DRAWINGS

FIGS. 3A-3C show the cell viability of HTC273, HTC245, and HTC264, respectively, cells before and after packaging and shipping.

FIGS. 4A-4C show the secretion of IFN-γ of HTC273, HTC245, and HTC264, respectively, cells before and after packaging and shipping.

FIGS. 8A-8C show the secretion of IFN-γ of HTC273, HTC264, and HTC245, respectively, cells and formulated for ID, IT and IV administration.

FIGS. 9A-9C show the expression of CD40L of HTC273, HTC264, and HTC245, respectively, cells formulated for ID, IT and IV administration and stored for 24 and 48 hours.

FIGS. 10A-10C show the secretion of IFN-γ of HTC273, HTC264, and HTC245, respectively, cells formulated for ID, IT and IV administration and stored for 24 and 48 hours.

FIGS. 11A-11C show the viability of HTC273, HTC264, and HTC245, respectively, cells formulated for ID, IT and IV administration and stored for 24 and 48 hours.

FIG. 15A-15C shows the CD40L expression for CAC and CFB after 48 hours for HTC245, HTC264, and HTC273, respectively.

DETAILED DESCRIPTION OF ILLUSTRATIVE EMBODIMENTS

Figure 1A:
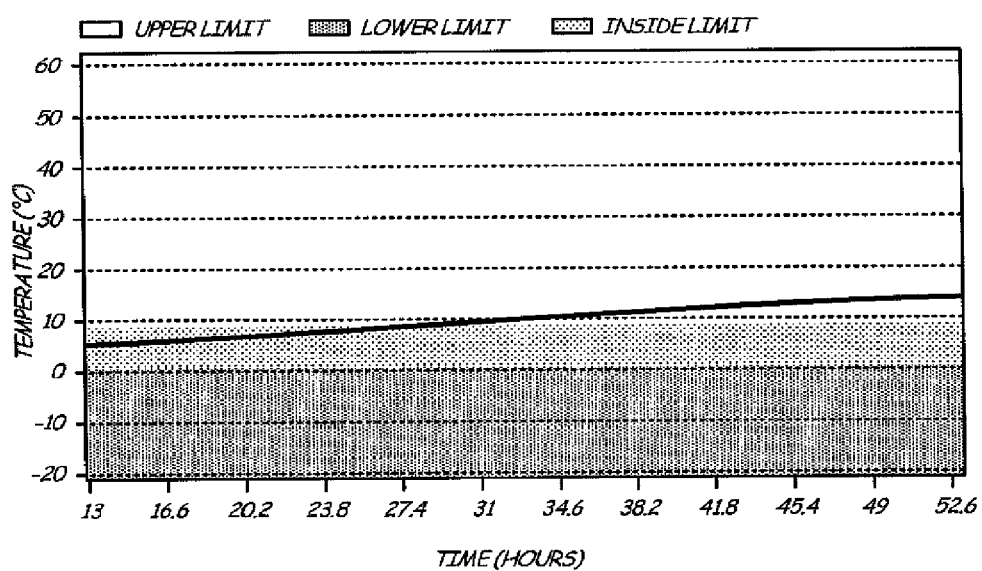
FIG. 1A is a plot of the temperature change in the container during transportation where the container was not preconditioned.

This invention relates to the packaging, storage and distribution of live cell biological drug products formulated in non-nutritive buffer that can exhibit cellular characteristics useful for immunotherapy even after extended periods of time. These live cell biological drugs can maintain viability as well as pre-determined identity and functional characteristics even after about 72 hours in the non-nutritive buffer.

In some exemplary embodiments, immune Th1 memory cells used as a biological drug product can maintain viability, retain pre-determined identity (CD4+, CD45RO+, CD40L$^{hi}$,)CD62L$^{lo}$) and recover functional criteria such as secretion of IFN-gamma>1000 pg/10$^6$ cells/4 h. These immune Th1 memory cells can exhibit these cellular characteristics for up to at least about 72 hours when formulated in a non-nutritive buffer with CD3/C28-coated microbeads and maintained in a refrigerated state.

The biological products that include the living cells can be packaged in environmentally controlled conditions to maintain the desired storage conditions and shipped nearly anywhere in the world to points-of-care by an express courier service (e.g. Federal Express, United Parcel Service (UPS), and similar international couriers). Preferably, the package with the living cells is stored and transported under refrigeration temperatures. At the point-of-care, the formulated cells can be removed from the package and administered to a patient. The formulated cells remain stable after removing from the refrigerated packaging for up to about 6 hours. Preferably, the cells are first removed from refrigerated packaging at the point-of-care and allowed to equilibrate to room temperature from 1-2 hours prior to patient administration. The transported cells are surprisingly stable and can be used for similar methods as cells that were not stored for extended periods of time. Alternatively, the cells are stored and transported in a frozen state to a point-of care. The cells can be stored in a frozen state at a point-of-care and be formulated in an automated or semi-automated closed, sterile system and then stored on-site in a refrigerated state for up to about 72 hours before administration to a patient.

Living cells can be any cell that is more than minimally manipulated as that term is used by the FDA to determine that the cell product is a biological drug requiring evaluation in humans only under an Investigational New Drug (IND) Application or equivalent and manufactured under Good Manufacturing Practices (GMP) in accordance with 21 C.F.R. parts 211, 606 and 820 as applicable.

The living cells can be of a single type or a mixture as long as they have defined identity and functional criteria. The cells can be natural or engineered, derived from autologous, allogeneic and/or xenogeneic donors. While the living cells are the active ingredient of the biological drug, other substances can be added to the cells, such as biologically active proteins, peptides, chemicals, nucleotides (RNA, DNA) and/or devices. The cells can be freely suspended in formulation or attached to a surface or device or encapsulated in a device or material. The cells should be intended to treat or prevent the occurrence of a disease or condition. The cells can be infused, injected or implanted in any location of the body.

By functional characteristics, it is meant to include a variety of functions, particularly immune functions and differentiation functions performed by the cells and useful in immunotherapy and stem cell therapy. These immune functions can include, for example, secretion of molecules, expression of cell surface moieties, recognition of molecules, the ability to respond to molecules and grow and/or change into a particular cell type or cause other cells in the body to grow, change, die or in some manner alter the normal or disease function as well as other immunological and cell differentiation functions known in the art. The immunological functions can be processes, or cascades of processes or production of molecules that are involved in the innate and/or the adaptive immune system response or modulation of the adaptive or innate immune response. The functions may be related to cell mediated immunological functions and/or to the humoral system, both immunostimulatory and immunosuppressive functions. The functional characteristics may be related to immunological memory or related to distinguishing between self and non-self antigens, or recognition of pathogens, such as bacteria, viral or fungus as well as tumors or other abnormal or undesired cells or tissues. Other functions may be related to surface molecules which mediate such functions as trafficking to a particular organ or tissue or location, surface molecules that block, promote or otherwise modulate immune responses or enable the differentiation to a particular cell type.

This disclosure describes biological drug products that include living cells formulated in non-nutritive buffer as the active ingredient. In some embodiments, the cells are living immune cells that can be used for immunotherapy or stem cell therapy. The compositions are stable in non-nutritive buffer for at least about 6 hours at room temperature and for at least about 24, preferably at least about 48, and more preferably at least about 72 hours at refrigeration temperatures. Surprisingly, the live cells in the compositions can maintain their identity, viability and functional characteristics that they exhibited in nutrient containing media even after formulation into non-nutrient buffer. The compositions described herein can be packaged and advantageously be shipped and distributed using commercial couriers in containers that maintain the appropriate storage conditions from a processing facility to a point of care. Such capabilities can result in substantial savings of labor, time and money in production and administration of therapeutic compositions containing live cells. Furthermore, accessibility of live cell therapeutic compositions for patients is greatly enhanced since a processing facility can produce, package and distribute the cells to any point of care site in the world.

This disclosure also describes methods of maintaining live cell suspensions for extended periods of time in non-nutritive buffer. The methods include transferring the live cells into non-nutritive buffer and storing them at a cooler storage temperature. In some embodiments, the live cell compositions are stored under refrigeration conditions. When desired, the compositions are removed from storage and placed at room temperature for a period of time. In some embodiments, the functional characteristics of the live cells are substantially recovered after the live cell suspensions have been placed at about room temperature for a period of time. In other embodiments the functional characteristics of the live cells are substantially recovered after the live cell suspensions have been placed in physiological conditions for a period of time.

The therapeutic compositions described herein include live cells. By live cells, it is meant that>70% of the cells are viable as determined by appropriate assay techniques such as trypan blue extrusion, MTT or bioluminescent detection of the ATP levels such that the cells are capable of ex vivo manipulations such as expansion, differentiation, and/or activation under appropriate conditions. The compositions, however, may include some inactivated cells, radiated cells and/or non-viable cells. The live cells may be derived from a number of sources including, for example, immortalized cell lines, primary cell cultures, biological fluids, tissues, cord blood, peripheral blood, bone marrow, frozen aliquots of cells and the like. Live cells derived from other sources that are capable of ex-vivo manipulations as described above are also within the scope of the invention.

The cells in the therapeutic composition can be allogeneic cells. Cells derived, for example, from blood or marrow of allogeneic donors may be processed in a desired manner and then formulated for infusion into a patient. The infusion formulation placed in a syringe or transfer pack or other suitable device for holding human use products can be packaged and shipped to the point of care site for patient administration. Alternatively, the cells in the therapeutic composition may be autologous cells that have been manipulated, formulated, packaged and shipped and are to be reinfused into the same patient. The living cells may also be derived from a non-human source and have been manipulated, fotmulated, packaged and shipped for human administration (xenogeneic). The same therapeutic compositions described for human administration can also be used in non-human therapeutic and disease prevention settings.

In an embodiment where the live cells in the compositions are immune cells, these immune cells can include cells derived from bone marrow or cord blood, granulocytes, such as neutrophils, basophils, and eosinophils. The immune cells can also be monocytes, macrophages, dendritic cells, natural killer cells, lymphocytes including B-cells, T-cells and NKT cells. T-cells can be, for example, CD4+ cells (including Th0, Th1, Th2, Th17 and Treg cells) and/or CD8+ cells (Tc1 and Tc2).

One immunotherapy method for enhancing the cellular immune response in subjects is a type of cell therapy called adoptive immunotherapy. A cell therapy is a drug whose active ingredient is wholly or in part a living cell. Adoptive immunotherapy is a cell therapy that involves the removal of immune cells from a subject, the ex-vivo processing (i.e., activation, purification and/or expansion of the cells) and the subsequent infusion of the resulting cells back into the same subject (autologous therapy) or into a different subject (allogeneic therapy).

The biological drug product can include live cells that have been manipulated using a variety of ex vivo manipulations for adoptive immunotherapy. Live cells that have been manipulated ex vivo can include, for example, LAK cells (Rosenberg U.S. Pat. No. 4,690,915), TIL cells (Rosenberg U.S. Pat. No. 5,126,132), cytotoxic T-cells (Cai, et al U.S. Pat. No. 6,255,073; Celis, et al. U.S. Pat. No. 5,846,827), expanded tumor draining lymph node cells (Terman U.S. Pat. No. 6,251,385), various preparations of lymphocytes (Bell, et al U.S. Pat. No 6,194,207; Ochoa, et al. U.S. Pat. No 5,443,983; Riddell, et al. U.S. Pat. No. 6,040,180; Babbitt, et al. U.S. Pat. No. 5,766,920; Bolton U.S. Pat. No 6,204,058), CD8+ TIL cells (Figlin et al. (1997) Journal of Urology 158:740), CD4+ T-cells activated with anti-CD3 monoclonal antibody in the presence of IL-2 (Nishimura (1992) J. Immunol. 148:285), T-cells co-activated with anti-CD3 and anti-CD28 in the presence of IL-2 (Garlic et al. (1999) Journal of Immunotherapy 22:336) antigen-specific CD8+ CTL T-cells produced ex-vivo and expanded with anti-CD3 and anti-CD28 monoclonal antibodies (mAb) in the presence of 1L-2 (Oelke et al. (2000) Clinical Cancer Research 6:1997), and injection of irradiated autologous tumor cells admixed with Bacille Calmette-Guerin (BCG) to vaccinate subjects followed seven days later by recovery of draining lymph node T-cells which are activated with anti-CD3 mAb followed by expansion in IL-2 (Chang et al. (1997) Journal of Clinical Oncology 15:796).

In one exemplary embodiment, the therapeutic composition of this disclosure includes at least some T-cells, preferably allogeneic T-cells. These T-cells are also preferably activated through cell surface activation to form activated Th1 memory cells. The T-cells may be activated in a variety of ways including by the use of immobilized monoclonal antibodies specific for T-cell surface molecules. Suitable activated T-cells are, for example, described in U.S. Pat. No. 7,435,592 and incorporated herein by reference. The cells preferably have cell surface moieties that are cross-linked by monoclonal antibodies or other binding agents. These monoclonal antibodies and/or binding agents are preferably cross-linked by, for example, immobilization on a solid surface in order to activate the T-cells. These are referred to herein as cells activated in culture (CAC). These ex viva prepared CAC can be frozen for future use or formulated for infusion.

In preferred embodiments, the ex vivo prepared CAC are stored frozen until needed for patient administration. Prior to administration to the patient the CAC are thawed, washed and reactivated in nutrient media by cross-linking of the cell surface binding moieties such as CD3 and CD28 as described, for example in U.S. Pat. No. 7,402,431 which is incorporated herein by reference. The CAC, together with the cross-linking agent, can then be washed and transferred to a non-nutritive buffer such as a formulation buffer. The reactivated cells in formulation buffer are referred to herein as cells in formulation buffer (CFB). The CFB can be administered to the patient for therapeutic purposes. Generally, these reactivated cells, once transferred to non-nutritive buffer have a limited shelf life. Living cells can be formulated at a density of at least about $10^6$ cells per ml, preferably at about $10^7$ cells per ml or higher. In some embodiments, the living cells may be formulated at a density at about $10^8$ cells per ml or higher. The specific concentration of the cells may be determined by the specific use of the cells and the therapy protocol.

The therapeutic composition may also include a number of other components. These components can include, for example, agents that maintain the live cells in the desired activation state. In one exemplary embodiment, the therapeutic composition can include agents that maintain the T-cells in an activated state such as Dynabeads ClinExVivo™ described below in the Examples.

The present invention includes methods of storing and handling the live cell compositions to increase the shelf life. Shelf life as used herein is defined as the amount of time after formulation that the CFB maintain viability, pre-defined identity and functional characteristics. Generally, the cells are transferred to non-nutritive buffer that is appropriate for infusion into a patient. The cells can be in a variety of non-nutritive buffers. Non-nutritive buffer, as referred to herein, is any type of media, buffer or other liquid that lacks the appropriate components to support cellular proliferation and/or expansion. The non-nutritive buffers generally are isotonic, USP sterile, pyrogen-free and contain the appropriate components and/or buffering system to maintain live cells intact and are licensed for human parenteral use. In an exemplary embodiment, the non-nutritive buffer is a formulation buffer that is Plasmalyte A (Baxter Scientific, Deerfield, Ill.) with 1% human serum albumin. (McKesson, San Francisco, Calif.)

In embodiments with activated cells, particularly activated Th1 cells, the activation signals for the cells are maintained even when the cells are transferred to the non-nutritive buffer. For example, in embodiments where the cells are activated by cross-linking the cell surface binding moieties, the cross-linking is preferably maintained in the non-nutritive buffer. The maintenance of the cross-linking during storage can be critical to restoring the functional characteristics of the composition after removal from storage. Cell compositions in which the activating components are removed in non-nutritive buffer do not recover in the same manner as the cells that have maintained the activated state.

The methods described herein also include the handling of the live cells after the cells are transferred into a non-nutritive buffer. The live cell composition can be transferred to an environment with a cooler temperature for storage in order to increase the shelf life of the compositions. The cooler temperature to which the cells in non-nutritive buffer are transferred to is referred to herein as the storage temperature. The cells are generally transferred to the storage temperature as quickly as possible after being placed in the non-nutritive buffer. The cells are preferably transferred to the storage temperature in less than about six hours after being placed in non-nutritive buffer, more preferably in less than about four hours after being placed in non-nutritive buffer. In even more preferred embodiments, the cells are transferred to the storage temperature in less than about one hour after being placed in the non-nutritive buffer.

The storage temperature at which the compositions can be held varies but is generally below physiological temperature i.e. below at about 37° C. Preferably, the cells are stored at refrigeration temperatures. Refrigeration temperatures can be between the range of about −2° C. and about 12° C. More preferably, the cells are stored at a temperature between above 0° C. and about 10° C. Most preferably, the cells are stored between about 4° C. and about 8° C.

The compositions described herein may also be packaged, shipped and distributed from a manufacturing or processing facility to a point of care site. A manufacturing or processing facility can be a facility such as a hospital, clinic or any production facility capable of handling living cells for biological drugs in compliance with established guidelines. A point of care can be a hospital, clinic or any other site at which a patient is generally administered care. The compositions are generally packaged for shipping in a manner that maintains the compositions within the storage temperature range stated above. The cells can be stored and shipped in a variety of containers. The cells can be stored and shipped in, for example, a flexible container, syringe and the like. When shipping, the container such as a syringe can be placed in a package such as an insulated box. The package or box is, preferably, preconditioned at the desired storage temperature prior to the container with the live cells being placed in the package. The compositions, for example, can be packaged in ice or aerogel packed boxes. The packages are preferably insulated boxes that are able to maintain the desired storage temperatures, regardless of the external temperature. The boxes are also preferably preconditioned, meaning they have been stored or set at the desired temperature prior to container with the living cells being placed inside. In preferred embodiments, the packages are preconditioned prior to placement of the biological product and packages are transported under refrigeration or freezing conditions to the point of care. Any type of shipping method may be used but in exemplary embodiments shipping is by commercial couriers.

The shelf life of the compositions described herein can be surprisingly extended when the compositions are stored within the storage temperature range. The shelf life of the live cell compositions can be extended for greater than about 6 hours. Preferably, the shelf life of the live cell compositions can be extended for greater than about 24 hours, and more preferably for greater than about 48 hours. In even more preferred embodiments, the shelf life of the compositions can be extended for up to about 72 hours. In the most preferred embodiment, the shelf life can be extended for up to about 120 hours. Shelf lives of greater than about 120 hours are also within the scope of this invention.

The cellular compositions in non-nutritive buffer stored according to the methods described herein can maintain their viability, identity and function during the storage period and after removal from storage. The viability of the cells can be determined by a variety of methods known in the art include assay techniques such as trypan blue extrusion, MTT, 7-Amino-Actinomycin D or bioluminescent detection of the ATP levels.

The identity of the cells can be confirmed by a variety of methods. The cells can be assayed for a variety of external and internal cell markers that are indicative of the particular cell type in the composition. External markers are categorized by the Cluster designation of monoclonal antibodies (cluster of differentiation (CD) designated from 1st to $8^{th}$ workshops on international human leukocyte differentiation antigens with total number of (247) CDs. Leukocytes express distinct assortments of molecules on their cell surfaces, many of which reflect either different stages of their lineage-specific differentiation or different states of activation or inactivation. Leukocyte cell surface molecules are routinely detected with anti-leukocyte monoclonal antibodies (mAbs). Using different combination of mAbs, it is possible to chart the cell surface immunophenotypes of different leukocyte subpopulations, including the functionally distinct mature lymphocyte subpopulations of B-cells, helper T-cells (Th), cytotoxic T-cells (Tc), and Natural Killer (NK) cells.

Even after storage in non-nutritive media, the live cells in the composition exhibit the functional characteristics that were present prior to formulation in the non-nutritive media. Functional characteristics can include a variety of activities including, for example, expression of functional molecules such as CD40L, FasL, perforin and granzymeB, co-stimulatory molecules 4-1BBL, CD28, CTLA4, and TNF-related activation-induced cytokine (TRANCE), TWEAK, PD-1, B7 family, adhesion molecules such as the integrins, the cadherins, and the selectins and secretion of a variety of cytokines and chemokines and expression of receptors for these cytokines and chemokines. Cytokines and chemokines are redundant secreted proteins with growth, differentiation, and activation functions that regulate and determine the nature of immune responses and control immune cell trafficking and the cellular arrangement of immune organs. Cytokines can include, for example, IL2, IL3, IL4, IL5, IL6, GMCSF, IFN-gamma and the like.

In some embodiments, the functional characteristics are retained after formulation and throughout storage and the levels of the enzymes or the markers can be assayed soon after removal from storage and shipping. For example, the CD40L expression can be assayed after the compositions are removed from storage and allowed to incubate at RT for about 2 hours. The CD40L expression can be similar to the levels of CD40L expression at the time of formulation and storage. See, for example, FIGS. 2A-2C. Similarly, the number of viable cells in the compositions can be determined after removal from storage and incubation at RT for about 2 hours. The number of viable cells can be similar to the cell viability levels at the time of formulation and storage. See, for example, FIGS. 3A-3C.

In other embodiments, the functional characteristics can be recovered after the cells are exposed to physiological conditions. This can indicate that the cellular compositions, upon infusion into a patient, can function as intended and secrete or express components characteristic of the cells at the time of formulation. The secretion of IFN-γ, for example, can be depressed when the cells are formulated and placed in storage. IFN-gamma may be referred to herein as IFN-γ or IFN-g. The return of the cells to room temperature does not restore the secretion of IFN-g but incubating the cells at 37° C. for 24 hours increases the secretion of the IFN-γ to levels similar to the levels at the time of formulation. See, for example, FIGS. 12D, 13D and 14D. Advantageously, the decrease in the IFN-γ levels during storage can prevent exhaustion of cellular resources. If the cellular resources for secretion are sufficiently preserved during storage, then the cells generally can restart the secretion of the IFN-γ under appropriate physiological conditions. Thus, administration of the composition to a patient can then still provide the patient with the IFN-γ and other inflammatory cytokines derived as a result of the administration of the therapeutic composition, even though the composition has been stored for an extended period of time prior to administration.

Extension of the shelf life of the compositions can be demonstrated in a variety of ways. As used herein, extension of shelf life can refer to the live cells in the compositions maintaining their viability, identity and their functional characteristics even after the extended storage times described above. Generally, after storage for at least 24 hours, the compositions maintain at least about 50 percent of the activity of a defining characteristic in non-nutritive buffer relative to the activity at the time of formulation. Preferably, at least about 75 percent and more preferably, at least about 85 percent and even more preferably, at least about 90 percent of the activity is maintained after storage relative to the activity at the time of formulation.

In preferred embodiments, after storage for at least 48 hours the compositions maintain at least about 50 percent of the activity of a defining characteristic in non-nutritive buffer relative to the activity at the time of formulation. Preferably, at least about 75 percent and more preferably, at least about 85 percent and even more preferably, at least about 90 percent of the activity is maintained after storage relative to the activity at the time of formulation.

In more preferred embodiments, after storage for at least 72 hours, the compositions maintain at least about 50 percent of the activity of a defining characteristic in non-nutritive buffer relative to the activity at the time of formulation. Preferably, at least about 75 percent and more preferably, at least about 85 percent and even more preferably, at least about 90 percent of the activity is maintained after storage relative to the activity at the time of formulation.

The cellular compositions can be administered to a patient using a variety of methods. The compositions may be administered intradermally, intravenously, intrathecally, intratumorally and the like.

EXAMPLES

Materials: PE-conjugated CD40L was purchased from Beckman Coulter, Brea, Calif. 7-Amino-Actinomycin D (7-AAD) (1000×) was purchased from Cayman Chemical Co., Ann Arbor, Mich. PlasmaLyte A was purchased from Baxter Scientific, Deerfield, Ill. Human serum albumin (HSA) was purchased from McKesson, San Francisco, Calif. FcR Binding Inhibitor was purchased from eBioscience, San Diego, Calif. Dynabeads ClinExVivo™ was purchased from Invitrogen, Carlsbad, Calif.

Preparation of Cells in Formulation Buffer (CFB)—Cells activated in culture media(CAC) were placed into cRPMI media for washing. Time was recorded to indicate the beginning of the formulation protocol. The cells in cRPMI media were centrifuged, the supernatant removed and the cells resuspended in cRPMI buffer. Cell viability was determined by using Trypan. Blue assays. The total cell number and the concentration of live cells were used to determine the percentage of viable cells. If the sample had greater than 80 percent cell viability, then the procedure was continued for reactivation and formulation of cells.

The CAC cells were resuspended at a concentration of $1 \times 10^7$ cells/ml. Reactivation was done at a live cell concentration of $1 \times 10^7$ cells/ml. Reactivation was done in a 24 well plate, 6 well plate or a 75 cm$^3$ flask depending on the volume. Dynabeads ClinExVivo™ CD3/CD28 were added to reactivate the cells and incubated at 36-38° C. and 5% $CO_2$ for 4 hours. After incubation for about 4 hours, then the cells were removed and transferred to a 50 ml. tube with final formulation buffer (FFB). FFB is PlasmaLyte A with 1% HSA. The reactivated cells were centrifuged, supernatant removed and resuspended in FFB. These are referred to as cells in formulation buffer (CFB).

CFB were resuspended in FFB at a concentration $10^7$ cells per ml. The CFB were resuspended for ID, IT or IV administration. 1 ml of the cell suspension was added to a 3ml syringe as an ID formulation. IT and IV formulation were 3 ml and 5 ml, respectively. The syringes with the appropriate formulations were stored in refrigeration with an average temperature of about 4° C.

Harvesting of samples after storage—The cells and supernatant were collected at different time points. The time points were as follows: 0(initial); 2 hours at Room Temp (RT); 48 hours at 4° C.; and 48 hours at 4° C. followed by 2 hours RT.

At each time point, 100 ul cell suspensions were collected and the cells were spun at 400 g for 5 min at 4° C. The supernatant was then transferred to another tube for IFN-γ detection later using ELISA. The cells were resuspended in 150 ul staining buffer for flow cytometry. In some experiments, the cells were resuspended in 100 ul cRPMI medium and cultured in the incubator at 37° C. for 24 h with 5% $CO_2$. The supernatant was taken after 24 h incubation and the IFN-γ was detected by ELISA.

Flow cytometry (CD40L and 7-AAD)—50 ul cell suspension were transferred from above (150 ul) into 3 eppendorf tubes, labeled as unstained, CD40L and 7-AAD, respectively. The unstained tube was incubated on ice for 20 min. For the CD40L tube, the cells were pre-incubated with FcR Binding inhibitor according to the instructions of the manufacturer for 20 minutes on ice. Then 40 ul staining buffer (PBS+1% FBS) and 10 ul PE-CD40L antibody was added into the cell suspension and incubated for additional 20 min on ice in the dark.

Cell viability was tested by flow cytometry of 7-AAD. 7-AAD intercalates into DNA of dead or damaged cells, thus determination of 7-AAD positive cells is an indicator of cell viability. For 7-AAD tubes, the tubes were centrifuged at 400 g for 5 min at 6C. After removing the supernatant, the cell pellets were resuspended in 100 ul 1×7-AAD solution. The tube was incubated on ice for 15 min in the dark. 1 ml of staining buffer was added to the CD40L tube and then the 3 tubes were centrifuged together. After discarding the supernatant, the cell pellets were resuspended in 0.4 ml staining buffer and FACS was run.

IFN-γ ELISA—The IFN-γ secreted in the supernatant was determined by IFN-γ sandwich ELISA kit (R&D Systems, Minneapolis, Minn.) according to the manufacturer instructions.

Example 1

This experiment was done to determine if cells in formulation buffer (CFB) are stable at low temperatures after transportation. Batches of cell suspensions were formulated in FFB and transported through a mailing service (Federal Express). The temperature was monitored by a data logger. The temperature change inside a box that was not preconditioned and a preconditioned Aerogel insulated box was monitored. The outside temperature was also monitored. Three different batches were formulated and transported. Supernatant samples were taken of cells activated in culture media (CAC), CFB right after formulation, CFB after 2 hours at Room Temperature (RT), CFB after 48 hours at 4° C., and CFB after 48 hours at 4° C. and 2 hours at RT. CAC was tested for expression of CD40L and the remaining cells were tested for expression of CD40L, and the viability of cells.

Figures 1B, 1C:
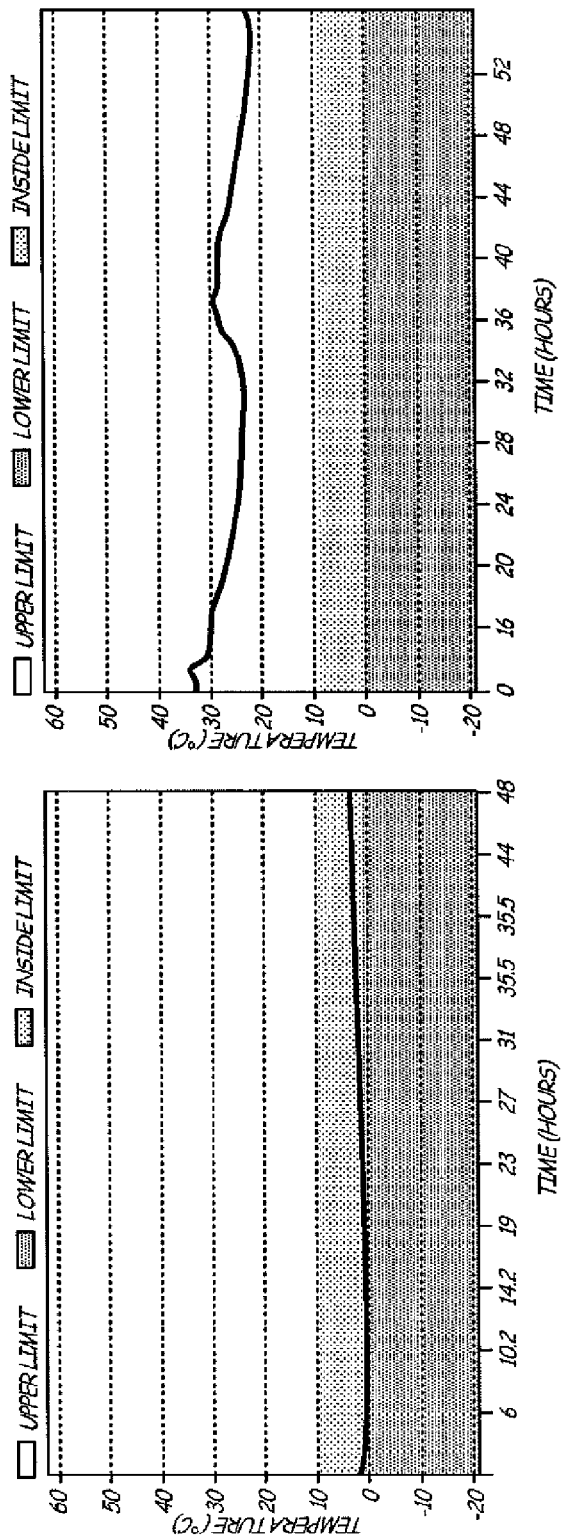
FIG. 1B is a plot of the temperature recorded inside the preconditioned aero gel insulated box.
FIG. 1C is a plot of the air temperature during transportation.

FIG. 1A and FIG. 1B shows the temperature that the cells were subjected to during transportation. FIG. 1A shows that the temperature varied from about 5° C. to about 13.7° C. within about 48 hours when the samples were not packaged in a preconditioned box. The samples were stable indicating a broader fluctuation of temperature is acceptable. FIG. 1B shows that the temperature inside the preconditioned and insulated box remains fairly stable. It varied from 0.2° C. to 2.2° C. FIG. 1C shows the variation of the outside temperature during the shipping period.

Figure 2A:
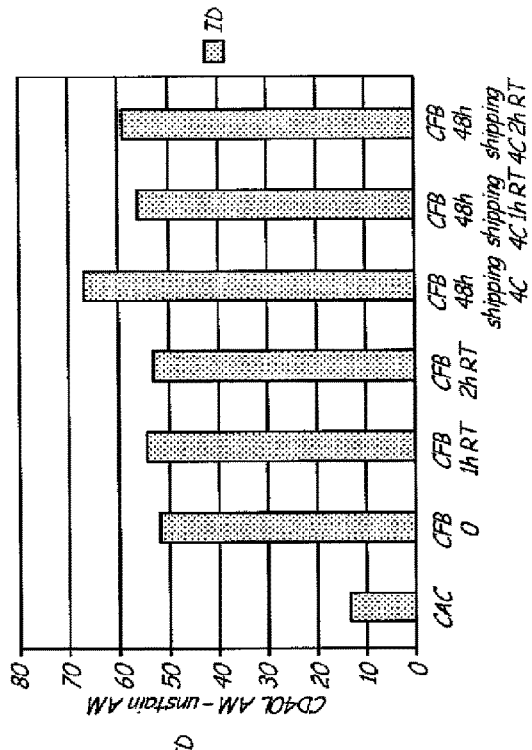
FIGS. 2A-2C show the expression of CD40L for HTC273, HTC245, and HTC264, respectively, cells before and after packaging and shipping.
Figure 2B:
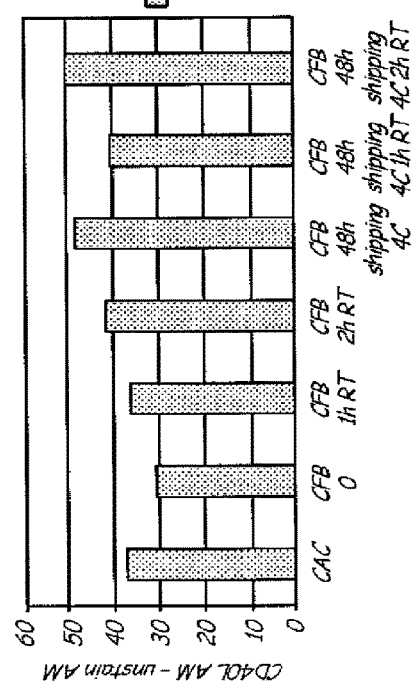
Figure 2C:
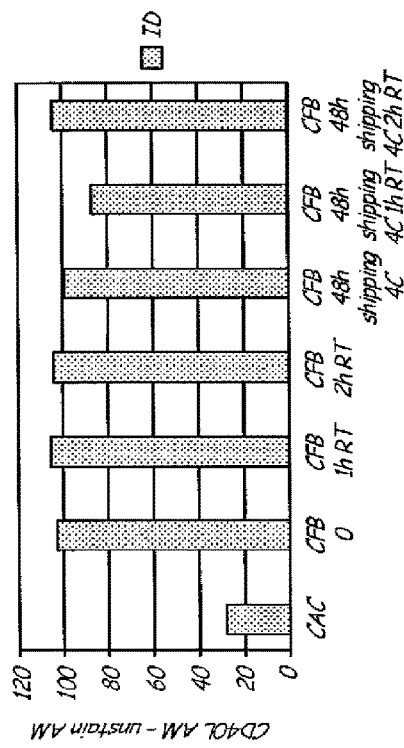
Figure 5A:
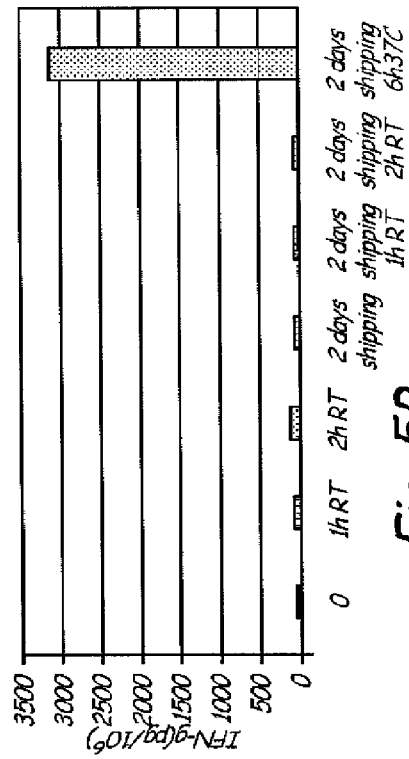
FIGS. 5A-5C show the secretion of IFN-γ of HTC273, HTC245, and HTC264, respectively, cells before and after packaging and shipping followed by incubation at 37° C. for 6 hours.
Figure 5B:
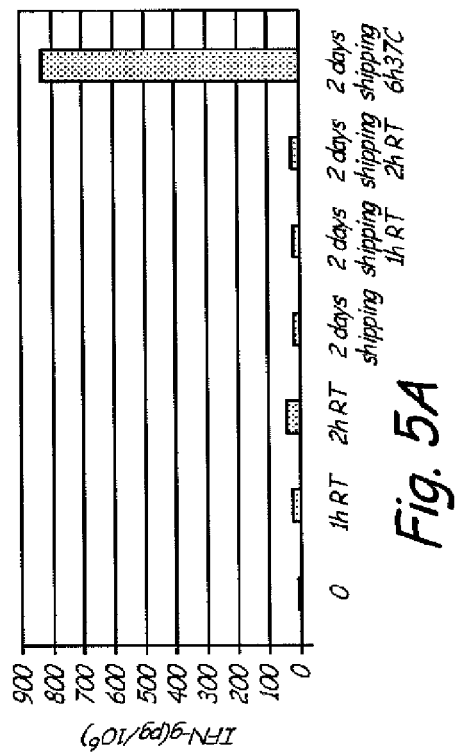
Figure 5C:
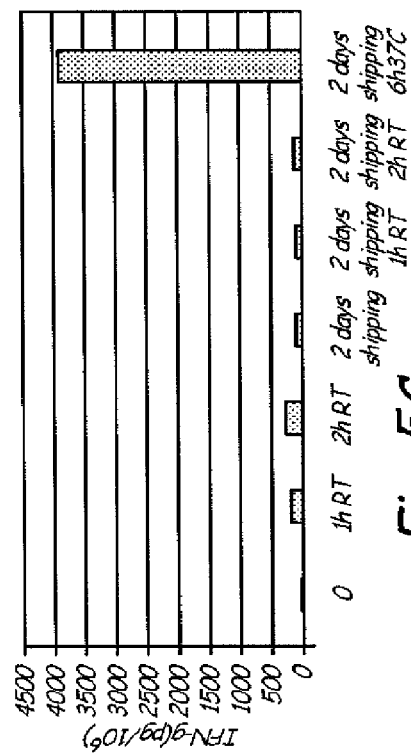
Figure 6A:
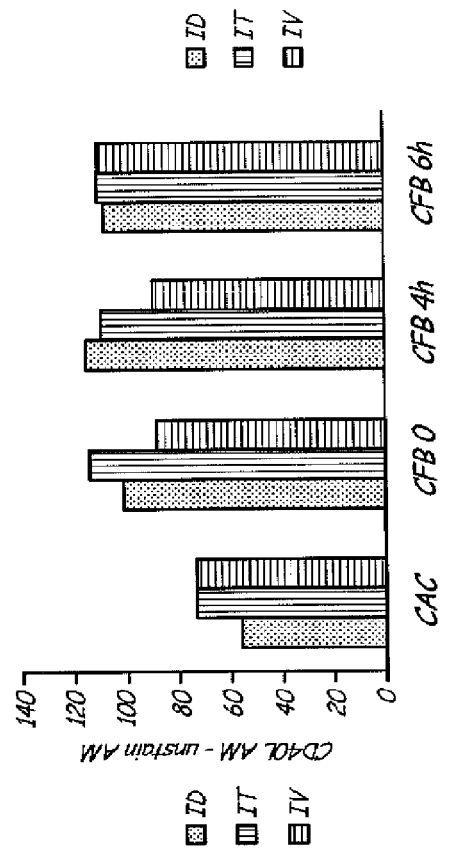
FIGS. 6A-6C show the expression of CD40L of HTC273, HTC264, and HTC245, respectively, cells and formulated for ID, IT and IV administration.
Figure 6B:
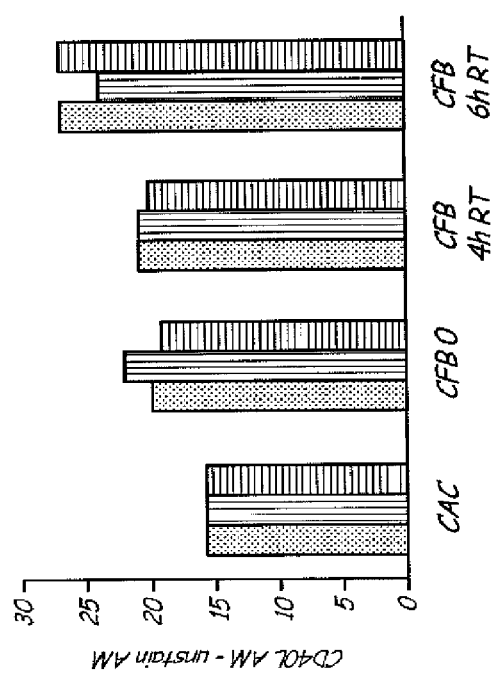
Figure 6C:
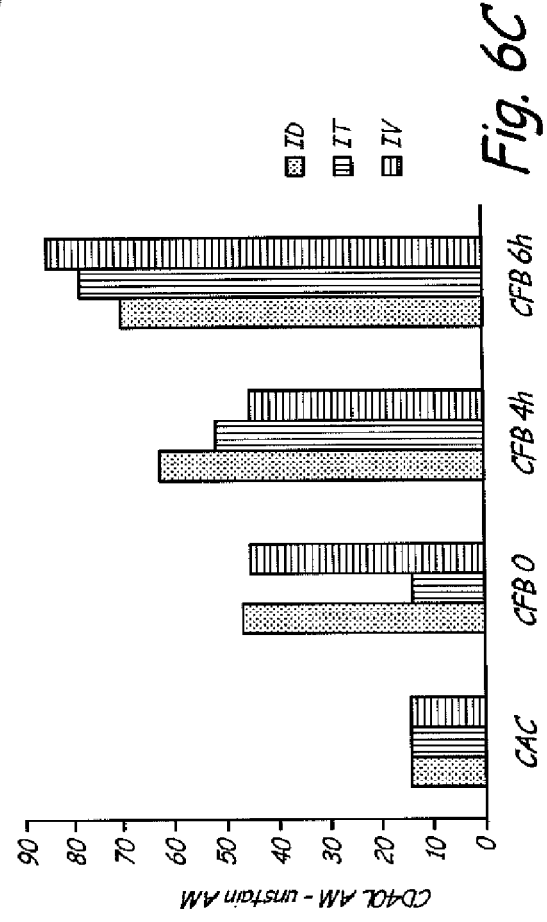
Figure 7A:
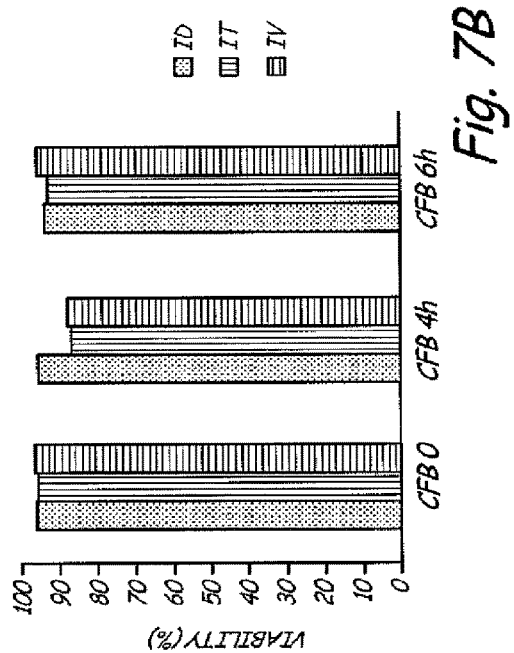
FIGS. 7A-7C show the cell viability for HTC273, HTC264, and HTC245, respectively, cells and formulated for ID, IT and IV administration.
Figure 7B:
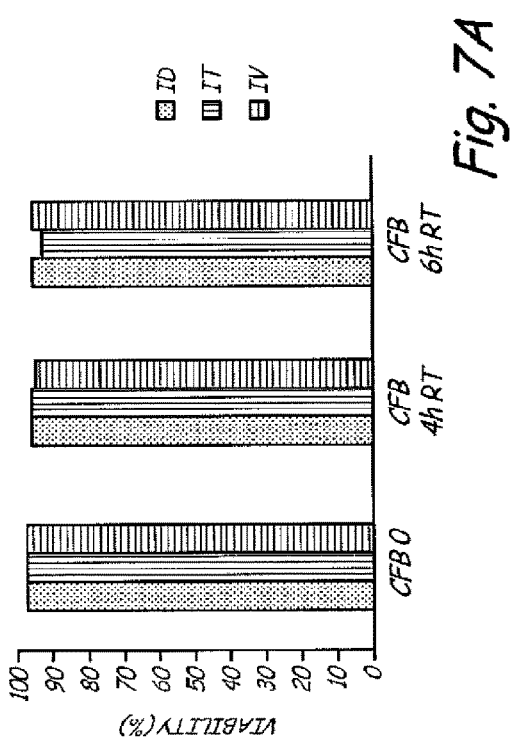
Figure 7C:
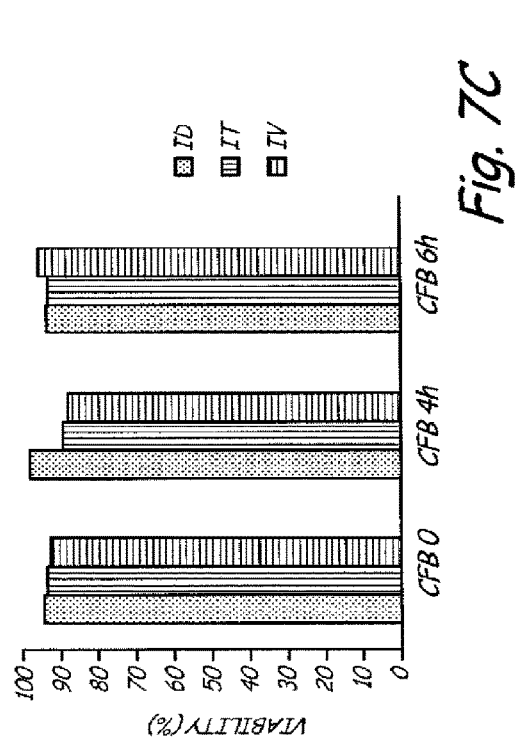

FIG. 2A-2C shows that the expression of CD40L did not change much. FIG. 3A-3C shows the cell viability after the shipping process is similar to the cell viability prior to shipping. These results indicate that keeping the therapeutic compositions within a broad range like about 2° C. to about 13° C. within the package was not detrimental.

Example 2

This study was performed to determine whether the low temperature can extend the expiration of CFB. The stability of different formulations of CFB at RT was performed. CFB were formulated for intradermal (ID), intratumoral (IT) or intravenous (IV) administration as described above. The stability of these formulations was tested to see if low temperature stability can be extended.

Batches HTC264, HTC245 and HTC273 were formulated for ID, IT and IV and tested for expression of CD40L, cell viability and secretion of IFN-γ for 6 hours at RT after formulation. FIG. 6A-6C, FIG. 7A-7C and FIG. 8A-8C show the results of these tests. All three of these parameters are stable after 6 hours at RT. FIG. 9A-9C shows that the expression of CD40L is stable after storage for 48 h at 4° C. FIG. 11A-11C indicates that the cell viability is stable after storage for 48 h at 4° C. FIG. 10A-FIG. 10C indicates that the IFN-γ secretion is does not recover as well after 48 hours at 4° C. However, as shown below this can be recovered by transferring back to RPMI and incubating at 37° C. for 24 hours.

Three batches (HTC264, HTC245 and HTC273) were formulated as ID, IV or IT formulations. 4 total syringes of each formulation were made (1 for RT, 1 for 24 h 4° C., 1 for 48 h 4° C., 1 for 72 h 4° C.) and incubated at 4° C. for different periods of time. The samples were collected after incubation back at RT for 2 hours. Table 1 below shows the timepoints, samples and tests that were performed for each batch of cells. IFN-γ levels were also determined when the cells were incubated at 37° C. for 24 hours.

TABLE 1

| Time | Samples | Test |
|---|---|---|
| −4 h | CAC | CD40L |
| 0 | CFB, supernatant | CD40L, IFN-γ, viability |
| 2 h | CFB, supernatant | CD40L, IFN-γ, viability |
| 24 h 4° C. | CFB, supernatant | CD40L, IFN-γ, viability |
| 24 h 4° C.-2 h RT | CFB, supernatant | CD40L, IFN-γ, viability |
| 48 h 4° C. | CFB, supernatant | CD40L, IFN-γ, viability |
| 48 h 4° C.-2 h RT | CFB, supernatant | CD40L, IFN-γ, viability |
| 72 h 4° C. | CFB, supernatant | CD40L, IFN-γ, viability |
| 72 h 4° C.-2 h RT | CFB, supernatant | CD40L, IFN-γ, viability |

Figure 12A:
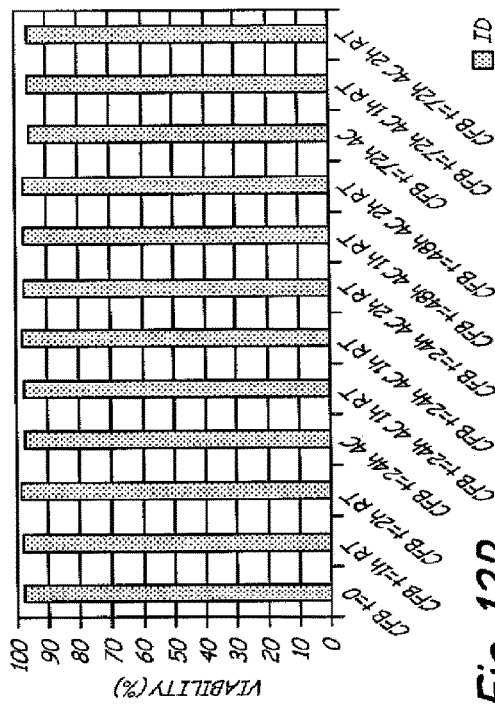
FIGS. 12A-12C show the expression of CD40L, viability of cells, IFN-γ by the HTC264 cells after 24, 48 and 72 hours of storage.
Figure 12B:
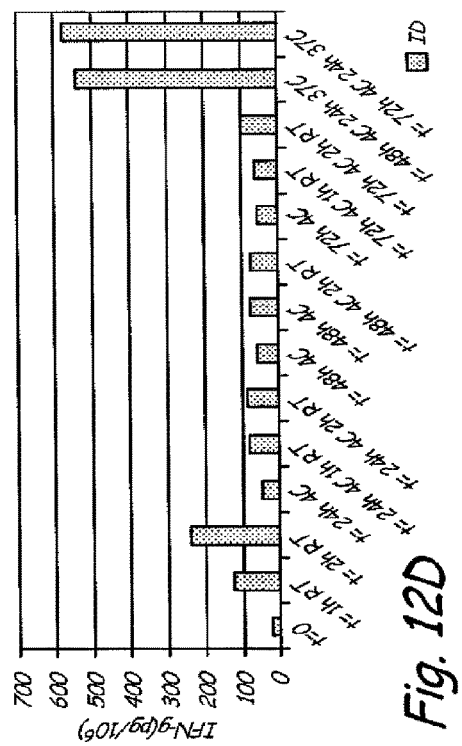
Figure 12C:
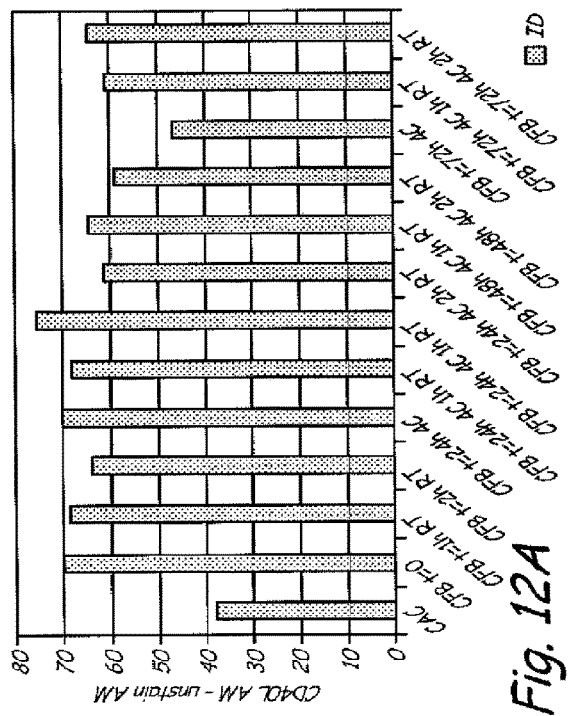
Figure 12D:
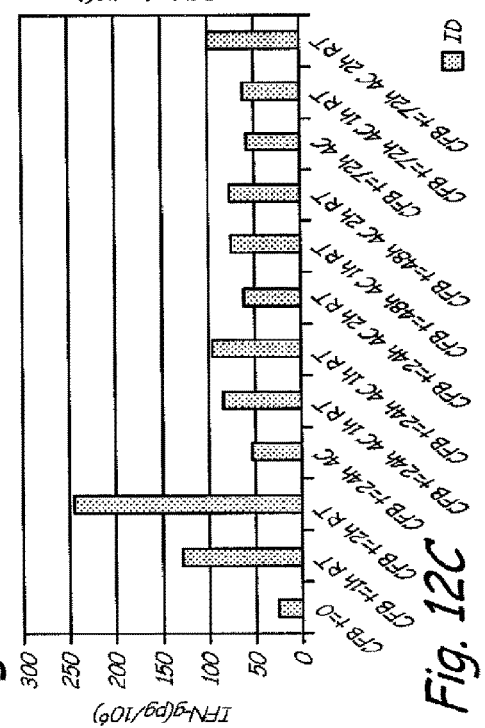
FIG. 12D shows the secretion of IFN-γ by the HTC264 cells after 72 hours of storage and incubation at 37° C. for 24 hours.
Figure 13A:
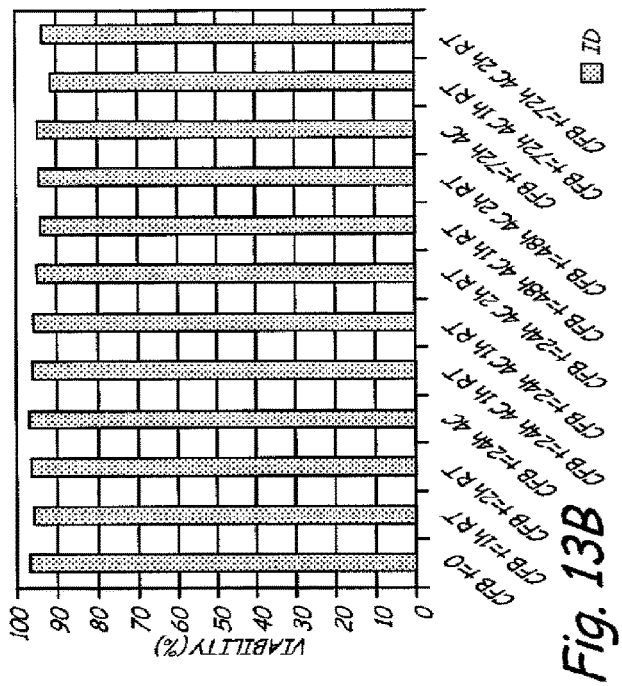
FIGS. 13A-13C show the expression of CD40L, viability of cells, IFN-γ by the HTC245 cells after 24, 48 and 72 hours of storage.
Figure 13B:
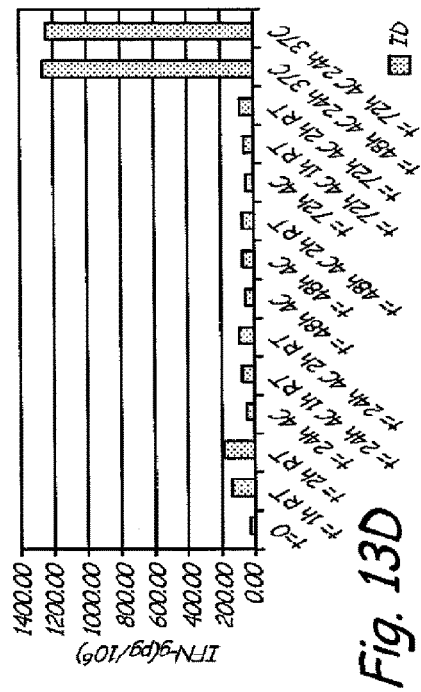
Figure 13C:
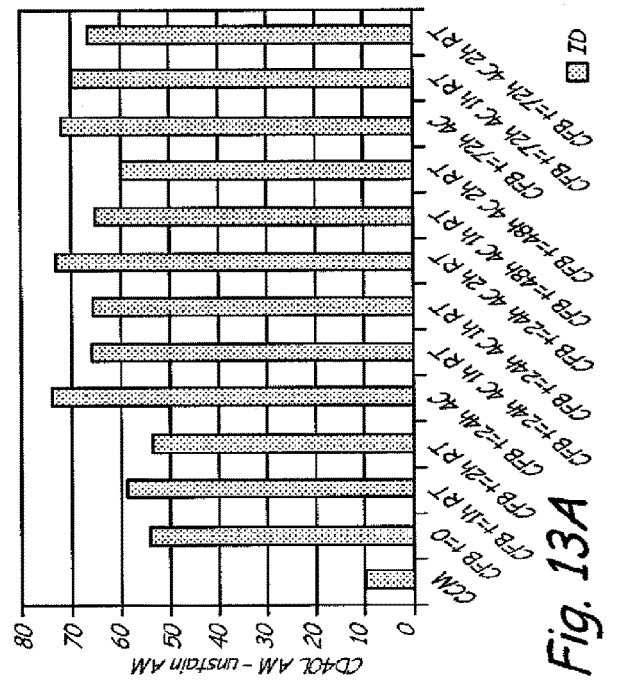
Figure 13D:
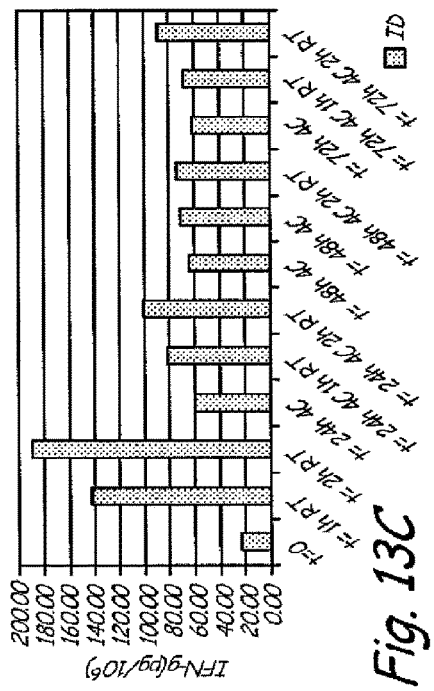
FIG. 13D shows the secretion of IFN-γ by the HTC245 cells after 72 hours of storage and incubation at 37° C. for 24 hours.
Figure 14A:
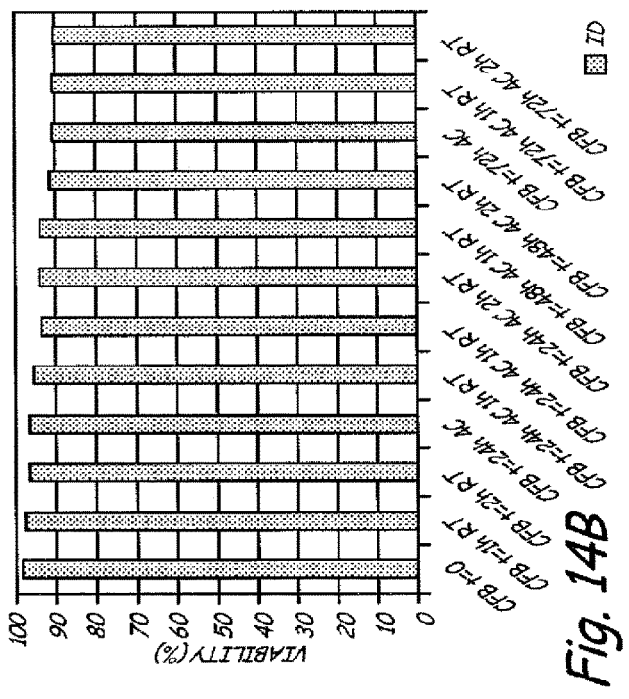
FIGS. 14A-14C show the expression of CD40L, viability of cells, IFN-γ by the HTC273 cells after 24, 48 and 72 hours of storage.
Figure 14B:
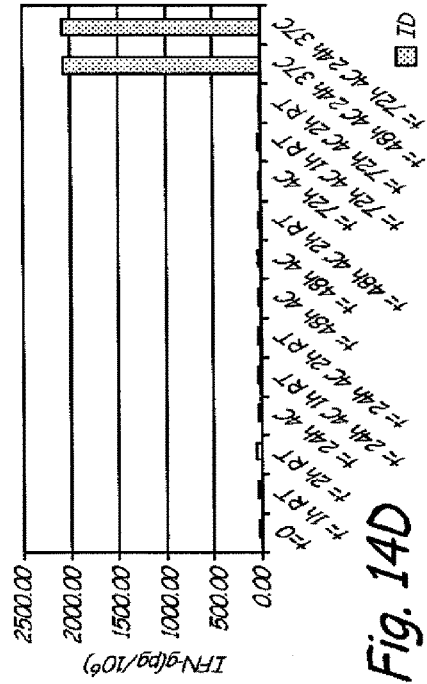
Figure 14C:
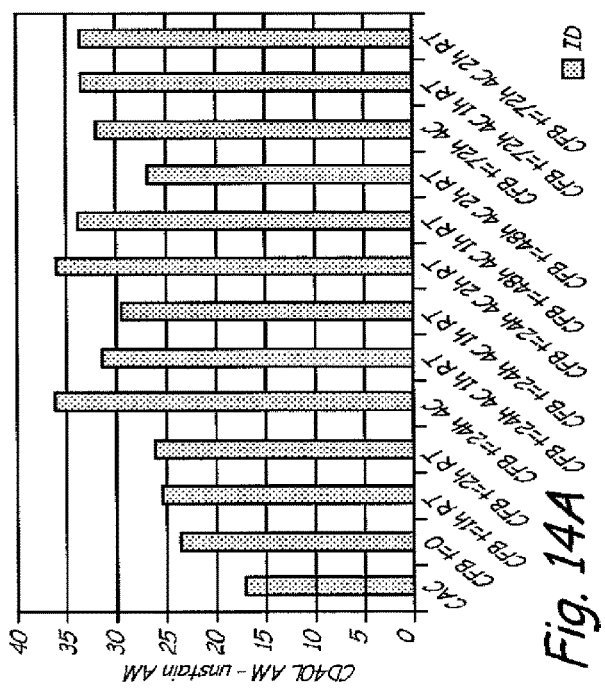
Figure 14D:
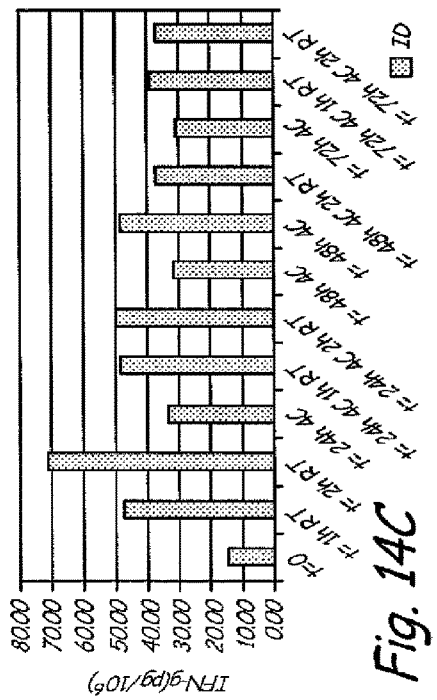
FIG. 14D shows the secretion of IFN-γ by the HTC273 cells after 72 hours of storage and incubation at 37° C. for 24 hours for 3 different batches of cells.
Figure 16A:
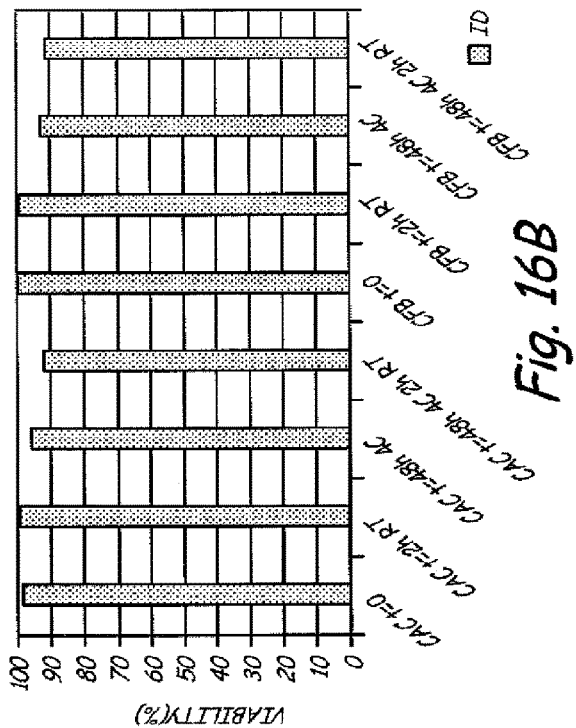
FIG. 16A-16C shows the cell viability for CAC and CFB after 48 hours for HTC245, HTC264, and HTC273, respectively.
Figure 16B:
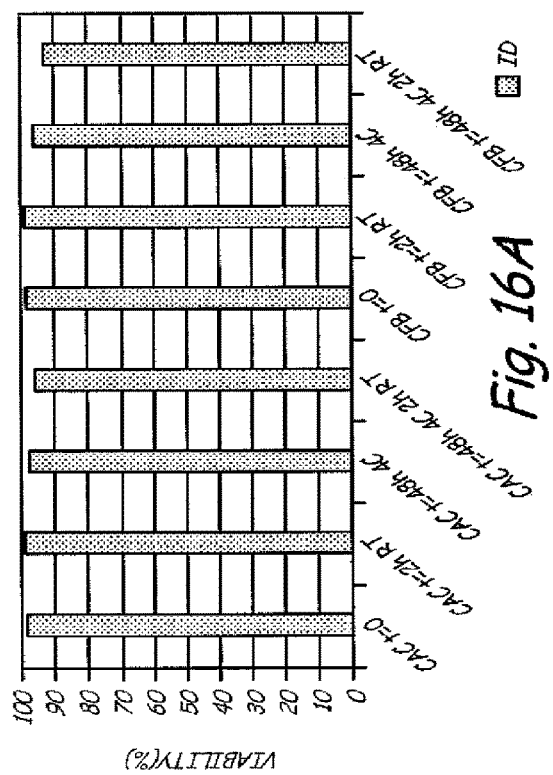
Figure 16C:
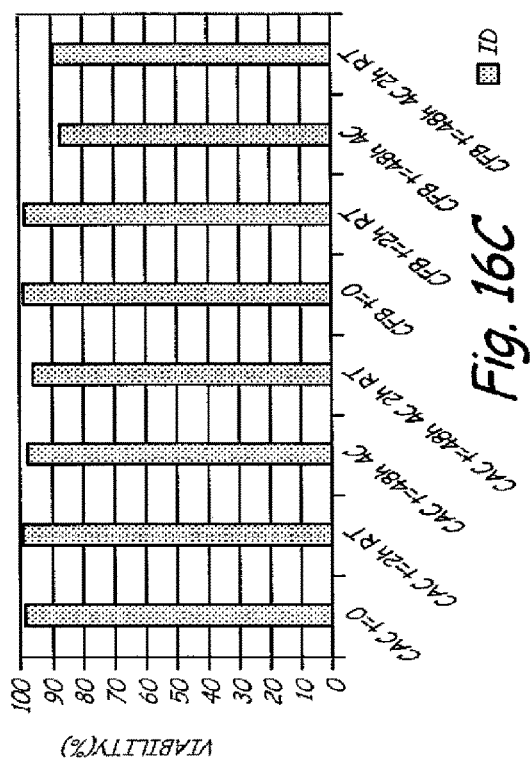
Figure 17A:
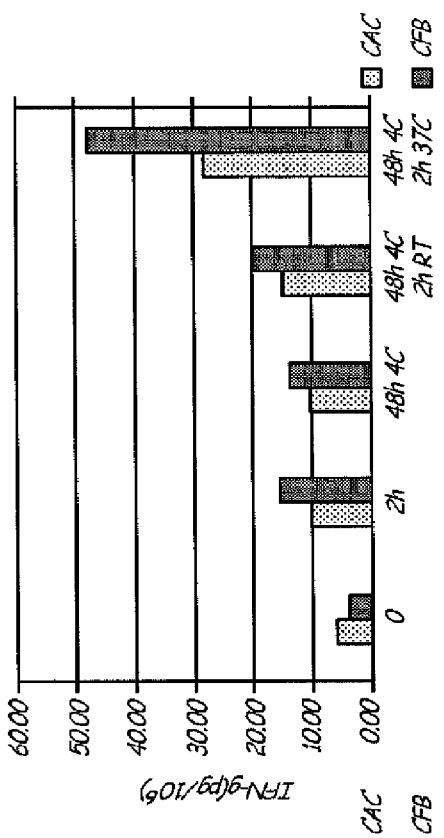
FIG. 17A-17C shows the secretion of IFN-γ for CAC and CFB after 48 hours HTC245, HTC273, and HTC264, respectively.
Figure 17B:
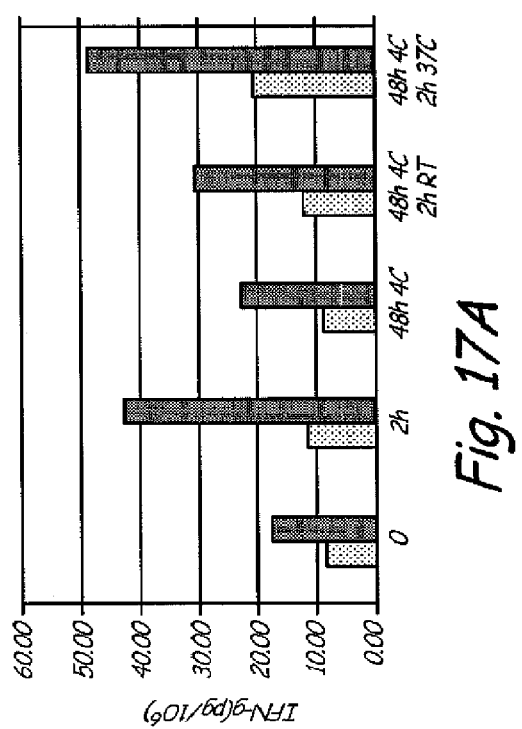
Figure 17C:
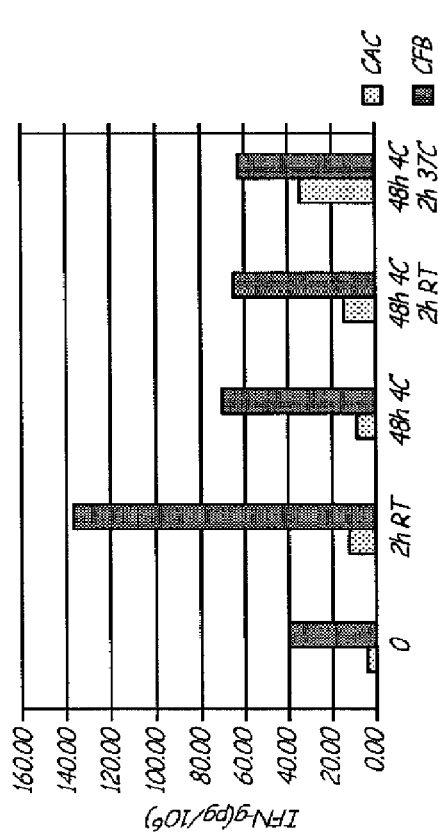

FIG. 12A-12D, FIG. 13A-13D and FIG. 16A-14D shows the results for batches HTC264, HTC245 and HTC273, respectively. Intradermal formulations of these batches were tested as indicated. The results showed that keeping the CFB at 4° C. can maintain the expression of CD40L on the cell surface even after 72 h (FIG. 12A, FIG. 13A and FIG. 16A). The cell viability was not affected much by low temperature storage (FIG. 12B, FIG. 13B and FIG. 16B). The IFN-γ secretion levels (FIG. 12C, FIG. 13C and FIG. 16C) are depressed when the cells are returned to RT for only 2 hours. However, the IFN-γ levels recover (FIG. 12D, FIG. 13D and FIG. 14D) when the cells are transferred back to RPMI media and incubated at physiological temperature (37° C.) for 24 hours. This indicates that the cells are still able to secret IFN-γ after keeping low temperature for 72 hours. This suggests that if these cells are administered therapeutically, the IFN-γ can be produced in the patient at similar levels to the cells that have not been subjected to lengthy storage.

Example 3

This experiment was done to compare the stability of the CAC cells and the CFB cells. Three different batches of cells were formulated as ID syringe. One syringe for CAC and one syringe for CFB for each batch. The CAC was thawed and washed with cRPMI. After cell counting, the cell pellet was resuspended in $10^9$ cells/ml with FFB and 1 ml of cell suspension was transferred into a 3 ml syringe. For CFB, the cell pellet was resuspended in $10^9$ cells/ml with cRPMI and mixed with the anti-CD3/anti-CD28 beads. The cell and bead mixture were incubated for 4 hours at 37° C. with 5% $CO_2$. The cells were washed with FFB and resuspended in $10^7$ cells/ml with FFB. The cell suspension was transferred into a 3 ml syringe. At each time point, 100 ul samples were obtained from the syringe for CD40L, IFN-γ, viability tests. After incubation at 4° C. for 48 hours, some samples were centrifuged at 400 g for 5 min. to remove the FFB. After discarding the supernatant, the cell pellet was resuspended in 100 ul cRPMI and incubated at 37° C. with 5% $CO_2$ for 2 hours. The supernatant was collected for IFN-γ detection. Table 2 below lists the samples that were collected and the tests that were performed.

TABLE 2

| Time | Samples | Test |
| --- | --- | --- |
| 0 | CAC, supernatant | CD40L, IFN-γ, viability |
| 2 h, RT | CAC, supernatant | CD40L, IFN-γ, viability |
| 48 h, 4° C. | CAC, supernatant | CD40L, IFN-γ, viability |
| 48 h 4° C.-2 h RT | CAC, supernatant | CD40L, IFN-γ, viability |
| 0 | CFB, supernatant | CD40L, IFN-γ, viability |
| 2 h, RT | CFB, supernatant | CD40L, IFN-γ, viability |
| 48 h, 4° C. | CFB, supernatant | CD40L, IFN-γ, viability |
| 48 h, 4° C.-2 h RT | CFB, supernatant | CD40L, IFN-γ, viability |

The results indicated that incubation of CAC for 4° C. for 48 hours decreased the CD40L expression on cell surface significantly See FIG. 15A-15C. However, incubation of CFB at 4° C. for 48 hours could maintain the CD40L expression suggesting that the crosslinking of CD3 and CD28 are essential for stability of the cells. CFB are able to maintain viability and secrete high amounts of IFN-γ, even after 48hour incubation at 4° C. See FIGS. 16A-C and FIGS. 17A-C.

Example 4

This study was performed to determine the stability of fog ululated CFB after packaging and shipment from a production facility in Jerusalem, Israel to a point-of-care. It was crucial to confirm that CFB product continues to meet pre-established identity and functional characteristics after 72 hours in transit, since at the end of the formulation process, the cells are transferred to a non-nutrient infusion buffer, in which the cells may lose their viability and unique identity and functional characteristics. It is known that low temperatures can slow down the gene expression and activity of cells and that this gene expression can be restored by returning cells back to physiological temperature. For this reason, the shipping is done using pre-validated, refrigerated, temperature-controlled containers.

The CFB cells were tested to check if their pre-defined identity and functional characteristics are kept after 72 hours in transit, by comparing the cells characteristics prior transit (at Baseline—formulated syringes after 4 h activation=FF) to those obtained after shipping to New York and back, at minimum 72 hours after FF completed.

The pre defined end point parameters were:
1. Viability test: CFB viability must be >70% live cells at all tested time points.
2. Rapid Endotoxin Test: endotoxin levels of sample collected at Baseline and after 72 h at 4° C. must be <0.5 Eu/ml.
3. Gram's Stain: no bacteria should be observed on the slide of samples collected at all tested time points.
4. Surface Staining—CD40L AM (CFB-CAC)
5. USP Sterility: no growth of the formulated sample in all tested mediums.
6. IFNγ secretion tested by ELISA:
   6.1 IFNγ accumulated during 4 hours activation >1000 pg IFNγ per $1\times10^6$
   6.2 IFNγ accumulated during 24 h after Baseline >6,000 pg per $1\times10^6$ cells
   6.3 IFNγ accumulated during 24 h after 72 h at 2° C.-8° C.>6,000 pg per $1\times10^6$ cells

RESULTS 3 separated Final formulation processes were performed on doses from batch HTC300.

The formulated product, packaged in syringes, was shipped with Flying Cargo (FC) to New York, and back to Jerusalem Israel.

Syringes in transit were kept at 2-8° C., from formulation end time up to 72 hours as was shown by temperature logger inside the shipping package. All the results are summarized in Table 3.

TABLE 3

| Formulation Number | Cell Type/Time | Cell Viability | CD40L AM CFB-CAC | IFNγ (pg/$10^6$ cells) | Endotoxin (EU/ml) | Gram's Stain | Sterility | Pass/Fail |
| --- | --- | --- | --- | --- | --- | --- | --- | --- |
| HTC300 T7-71+72 | CAC | 97.95% | | | | | | Pass |
| | CFB Baseline | 90.91% | 143.60 | 8,027 | <0.2 | Pass | Pass | |
| | After 24 hours at 37° C. in cRPMI | | | 45,741 | | | | |
| | after 72 h at 4° C. | 90.24% | 192.02 | | <0.277 | Pass | | |
| | After 24 hours at 37° C. in cRPMI | | | 28,955 | | | | |
| HTC300 T7-73+74 | CAC | 99.40% | | | | | | Pass |
| | CFB Baseline | 98.23% | 117.64 | 6,215 | <0.219 | Pass | Pass | |
| | After 24 hours at 37° C. in cRPMI | | | 31,155 | | | | |
| | after 72 h at 4° C. | 95.65% | 166.52 | | <0.208 | Pass | | |
| | After 24 hours at 37° C. in cRPMI | | | 13,284 | | | | |
| HTC300 T7-77+78 | CAC | 98.45% | | | | | | Pass |
| | CFB Baseline | 97.61% | 165.39 | 8,960 | <0.208 | Pass | Pass | |
| | After 24 hours at 37° C. in cRPMI | | | 42,520 | | | | |
| | after 72 h at 4° C. | 92.81% | 231.50 | | <0.2 | Pass | | |
| | After 24 hours at 37° C. in cRPMI | | | 22,583 | | | | |

As can be seen in Table 3, all three formulated batches passed all pre-defined acceptance criteria, hence demonstrating that CFB's stability in suggested distribution conditions.

Although the present invention has been described with reference to preferred embodiments, workers skilled in the art will recognize that changes may be made in form and detail without departing from the spirit and scope of the invention.

What is claimed is:

1. A method of handling a biological drug composition with living cells, the method comprising:
   formulating living CD4+ T-cells cells by reactivating the living CD4+ T-cells to a state of activation by cross-linking the CD3 and CD28 cell surface moieties by anti-CD3 and anti-CD28 monoclonal antibodies, wherein the living CD4+ T-cells have been activated by cross-linking CD3 and CD28 cell surface moieties by anti-CD3 and anti-CD28 monoclonal antibodies and wherein the living cells having been more than minimally manipulated, cryopreserved and thawed prior to reactivation;
   storing the reactivated living cells with the agents in the state of activation in a non-nutritive buffer at a storage temperature below about 20° C. for greater than 24 hours, wherein the reactivated living cells with the agents maintain a cell marker indicative of the living cells identity, maintain at least one functional characteristic exhibited by the living cells and are useful for immunotherapy after storage in the non-nutritive buffer for greater than about 24 hours in the state of activation in the non-nutritive buffer.

2. The method of claim 1 wherein the storage temperature is in a range between about 0° C. and about 10° C. and the reactivated living cells are stored for greater than 36 hours.

3. The method of claim 1 wherein the concentration of the cells in the non-nutritive buffer is about $10^6$ cells/ml or greater.

4. The method of claim 1 wherein the functional characteristic is expression of CD40L, FasL, perforin and granzyme B, expression of costimulatory molecules, expression of adhesion molecules, secretion of cytokines, chemokines or combinations thereof.

5. The method of claim 1 wherein the living cells in the composition express CD40L after storage in an amount of at least about 80% relative to the expression of CD40L at the time of formulation.

6. The method of claim 4 wherein the inflammatory cytokine secreted is IFN-γ and the level of secretion is in an amount of at least about 80% compared to the levels at the time of formulation.

7. The method of claim 6 wherein the secretion of IFN-γ after storage is recovered after incubation at 37° C. for at least 24 hours.

8. The method of claim 1 wherein the living cells in the non-nutritive buffer maintain at least about 50% of the activity of the functional characteristic for at least about 72 hours.

9. The method of claim 1 wherein the living cells are placed in a flexible container or syringe, wherein the flexible container or syringe is packaged in a temperature controlled device that maintains the living cells at the storage temperature.

10. The method of claim 9 further comprising shipping and distributing the package in the temperature controlled device to the point of care.

11. The method of claim 1 wherein the composition has at least about 80% viable cells after storage.

12. The method of claim 1 wherein the living cells in the non-nutritive buffer maintain at least about 50% of the activity of the functional characteristic for at least about 24 hours.

13. The method of claim 1 wherein the living cells in the non-nutritive buffer maintain at least about 50% of the activity of the functional characteristic for at least about 72 hours.

14. The method of claim 1 wherein the non-nutritive buffer is a formulation buffer comprising Plasmalyte A and 1% human serum albumin.

* * * * *